United States Patent [19]

Paget et al.

[11] 4,018,790

[45] Apr. 19, 1977

[54] SUBSTITUTED 1-SULFONYLBENZIMIDAZOLES

[75] Inventors: Charles J. Paget, Indianapolis; James H. Wikel, Greenwood, both of Ind.

[73] Assignee: Eli Lilly and Company, Indianapolis, Ind.

[22] Filed: Nov. 24, 1975

[21] Appl. No.: 634,942

Related U.S. Application Data

[63] Continuation-in-part of Ser. No. 574,202, May 8, 1975, abandoned, which is a continuation-in-part of Ser. No. 484,841, July 1, 1974, abandoned.

[52] U.S. Cl. ............... 260/309.2; 260/247.1 L; 260/293.6; 260/306.8 R; 260/306.8 D; 260/465 E; 260/471 R; 260/518 R; 424/248.5; 424/267; 424/273
[51] Int. Cl.² .................................. C07D 235/30
[58] Field of Search ....... 260/309.2, 293.6, 247.1 L

[56] References Cited

UNITED STATES PATENTS

| 3,825,537 | 7/1974 | Haugwitz et al. | 260/309.2 |
| 3,850,954 | 11/1974 | Widdig et al. | 260/309.2 |
| 3,853,908 | 12/1974 | Widdig et al. | 260/309.2 |

OTHER PUBLICATIONS

Widdig et al., Chem. Abst., 1973, vol. 79, No. 115,589x.
Widdig et al., Chem. Abst., 1973, vol. 79, No. 126500n.

*Primary Examiner*—Natalie Trousof
*Attorney, Agent, or Firm*—James L. Rowe; Everet F. Smith

[57] ABSTRACT

Certain 1-sulfonyl-2,5(6)-substituted-benzimidazole compounds are useful as antiviral agents.

23 Claims, No Drawings

SUBSTITUTED 1-SULFONYLBENZIMIDAZOLES

CROSS REFERENCE TO RELATED APPLICATION

This is a continuation-in-part of our copending application Ser. No. 574,202 filed May 8, 1975 which was a continuation-in-part of our copending application Ser. No. 484,841 filed July 1, 1974, both abandoned.

BACKGROUND OF THE INVENTION

The incidence of viral upper respiratory disease is immense. It has been estimated that nearly a billion cases annually appear in the United States alone. Studies performed in England (Tyrell and Bynoe, 1966) indicated that 74 percent of persons having colds were infected with rhinoviruses. Because more than 80 strains of rhinoviruses are already identified, the development of a practical rhinovirus vaccine is not feasible, and chemotherapy appears to be the more desirable approach.

The ability of chemical compounds to suppress the growth of viruses in vitro is readily demonstrated by using a virus plague suppresion test similar to that described by Siminoff, *Applied Microbiology*, 9(1), 66(1961).

It is the purpose of this invention to provide novel sulfonylbenzimidazle compounds which inhibit the growth of certain viruses, including 25 strains of rhinoviruses, polio (types I, II, III), Coxsackie (A9, A21, B5), echo virus (strains 1, 2, 3, 4) and Mengo virus. Rhinoviruses are known to be associated with the common cold. The compounds of the invention are potentially useful in the treatment of such virus infections in warm-blooded animals and humans.

Certain antifungal 1-dimethylaminosulfonyl-2-aminobenzimidazole compounds have been disclosed in German published application No. 2,206,010; published Aug. 16, 1973, and in U.S. Pat. No. 3,853,908.

Summary of the Invention

This invention provides pharmacologically useful sulfonyl benzimidazole compounds represented by Formula I

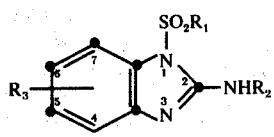

wherein
$R_1$ is $C_1$-$C_5$ alkyl, $C_3$-$C_7$ cycloaklyl, phenyl, furyl, thienyl, thiazol-2-yl, 2-acetamido-4-methylthiazol-5-yl, 1,3,4-thiadiazol-2-yl, 2-methyl-1,3,4-thiadiazol-5-yl, 2-methylamino-1,3,4-thiadiazol-5-yl or $R_4R_5NH$-, wherein $R_4$ and $R_5$ are independently $C_1$-$C_3$ alkyl and when taken together with the nitrogen atom to which they are attached, are pyrrolidino, piperidino or morpholino;
$R_2$ is hydrogen, formyl, acetyl or propionyl;
$R_3$ is $C_1$-$C_8$ alkoxycarbonyl, allyloxycarbonyl, propargyloxycarbonyl, ($C_3$-$C_7$ cycloalkyl)oxycarbonyl, ($C_3$-$C_7$ cycloalkyl)methyloxycarbonyl, 1-($C_3$-$C_7$ cycloalkyl)ethyloxycarbonyl, benzyloxycarbonyl, a-methylbenzyloxycarbonyl, phenoxycarbonyl, $C_1$-$C_8$ alkoxycarbonylmethyl, 1-($C_1$-$C_8$ alkoxycarbonyl)ethyl, hydrazinocarbonyl, carboxy, carboxamido, N-($C_1$-$C_4$ alkyl)carboxamido, N-($C_1$-$C_4$ alkoxy)-carboxamido, hydroxymethyl, cyano, methylsulfonyl or trifluoromethyl; and $R_3$ is at the 5 or 6 position.

DETAILED DESCRIPTION AND PREFERRED EMBODIMENTS

The present invention relates to new organic sulfonyl compounds that are useful as antiviral agents and to methods for their production. The compounds of the invention are prepared by reacting a tautomeric benzimidazole compound of the Formula II

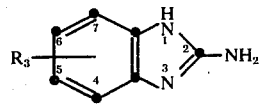

with a sulfonyl chloride compound having the formula $R_1SO_2Cl$ wherein $R_1$, and $R_3$ are as defined hereinabove to yield a compound according to Formula I wherein $R_2$ is hydrogen.

The term "tautomeric benzimidazole" refers to a benzimidazole reagent which can be substituted at either nitrogen atom with a hydrogen atom. The benzimidazole reactant, unsubstituted on nitrogen and bearing an $R_3$ substituent group at the 5 position of the benzene moiety, has a corresponding tautomeric form with which it is in equilibrium wherein the substituent resides alternatively at the 6 position. The isomer mixture can be indicated by numbering the alternate positions as 5(6). As a consequence of such tautomerism, the reaction of a 5(6) substituted benzimidazole with a sulfonyl chloride process isomeric mixtures of 5(6)-substituted sulfonylbenzimidazoles.

The following definitions refer to the various terms used throughout this disclosure. The term "furan" refers to the furan radical attached at the 2 or 3 position. The term "thienyl" refers to the thiophene radical attached at the 2 or 3 position. The term "thiazol-2-yl" or "2-thiazole" refers to the thiazole radical attached at the 2 position. The term "1,3,4-thiadiozole- 2-yl" or "thiadiazol-2-yl" refers to the 1,3,4-thiadiazole radical attached at the 2 position. The term "2-methyl-1,3,4-thiadiazol-5-yl" or "2-methylamino-1,3,4-thiadiazol-5-yl" refers to a 2-substituted-1,3,4-thiadiazole radical attached at the 5 position.

The term "$C_1$-$C_8$ alkyl" refers to the straight and branched aliphatic radicals of one to eight carbon atoms including methyl, ethyl, propyl, isopropyl, butyl, isobutyl, sec-butyl, tert-butyl, amyl, isoamyl, sec-amyl, sec-isoamyl (1,2-dimethylpropyl), tert-amyl (1,1-dimethylpropyl), neopentyl, hexyl, isohexyl (4-methylpentyl), sec-hexyl (1-methylpentyl), 2-methylpentyl, 3-methylpentyl, 1,1-dimethylbutyl, 2,2-dimethylbutyl, 3,3-dimethylbutyl, 1,2-dimethylbutyl, 1,3-dimethylbutyl, 1,2,2-trimethylpropyl, 1,1,2-trimethylpropyl, heptyl, isoheptyl (5-methylhexyl), sec-heptyl (1-methylhexyl), 1-ethylpentyl, 2,2-dimethylpentyl, 3,3-dimethylpentyl, 4,4-dimethylpentyl, 1,2-dimethylpentyl, 1,3-dimethylphenyl, 1,4-dimethylpentyl, 1,2,3-trimethylbutyl, 1,1,2-trimethylbutyl, 1,1,3-trimethylbutyl, octyl, isooctyl (6-methylheptyl), sec-octyl(1-methylheptyl), tert-octyl(1,1,3,3-tetramethylbutyl and the like. The term $C_1$-$C_8$ alkyl includes within its definition the terms "$C_1$-$C_3$ alkyl", "$C_1$-$C_4$ alkyl," $C_1$-$C_5$ alkyl," and "$C_1$-$C_7$ alkyl." The term "$C_1$-$C_8$ alkyl carbinol" refers to the straight and branched aliphatic alcohols in which alkyl group of one to eight carbon atoms as exemplified in the term "$C_1$-$C_8$ alkyl" above are substituted with an OH group. The term "$C_1$-$C_8$ alkoxy" includes ether radicals of one to eight carbon atoms such as methoxy, ethoxy, propoxy, isopropoxy, butoxy, isobutoxy, sec-butoxy, amyloxy, isoamyloxy, 1,2-dimethylpropoxy, tertanyloxy, neopentyloxy, hexyloxy, (2-methyl-1-pentyl)oxy, (4-methyl-2-pentyl)oxy, (2-ethyl-1-butyl)oxy, heptyloxy, 2-heptyloxy, octyloxy, 2-octyloxy, (2-ethylhexyl)oxy, isooctyloxy, (2,2,4-trimethyl-1-pentyl)oxy, and the like. The term "$C_1$-$C_8$ alkoxy" includes within its definition the term "$C_1$-$C_4$ alkoxy."

The term "$C_3$-$C_7$ cycloalkyl" refers to the saturated alicyclic rings of three to seven carbon atoms such a cyclopropyl, methylcyclopropyl, cyclobutyl, cyclopentyl, cyclohexyl, 1-, 2-, 3- or 4-methylcyclohexyl and cyclohepty. The term "$C_3$-$C_7$ cycloalkylmethyl" refers to a methyl radical substituted with saturated alicyclic rings of three to seven carbon atoms as exemplified in the term "$C_3$-$C_7$ cycloalkyl," such as cyclopropylmethyl, cyclobutylmethyl, cyclopentylmethyl, cyclohexylmethyl, cycloheptylmethyl and the like. The term "$C_3$-$C_7$ cycloalkyl alcohol" refers to cyclopropanol, cyclobutanol, cyclopentanol, cyclohexanol and cycloheptanol. The term "$C_3$-$C_7$ cycloalkylmethanols" refers to methanol substituted on the carbon with saturated alicyclic rings of three to seven carbon atoms; for example cyclopropylmethanol, cyclobutylmethanol, cyclopentylmethanol, cyclohexylmethanol, and cycloheptylmethanol. These $C_3$-$C_7$ alicyclic methanols are available from the corresponding $C_3$-$C_7$ alicyclic carboxaldehydes by reduction. The term "1-($C_3$-$C_7$ cycloalkyl)ethanol" refers to ethanols which are substituted on the carbon atom in the 1 position with saturated alicyclic rings of three to seven carbon atoms; for example, 1-cyclopropylethanol, 1-cyclopentylethanol, 1-cycloheptylethanol and the like. These ethanols are available from the corresponding 1-($C_3$-$C_7$ cycloalkyl)-methyl ketones by reduction. The term "1-($C_3$-$C_7$ cycloalkyl)-ethyl" refers to ethyl radicals substituted on the carbin atom in the 1 position with saturated alicyclic rings of three to seven carbon atoms. The term "$C_1$-$C_4$ alkyllamine" refers to aliphatic amines of one to four carbon atoms each as methylamine, ethylamine, propylamine, isopropylamine, butylamine, sec-butylamine and the like. The term "$C_1$-$C_4$ alkoxyamine" refers to methoxyamine, ethoxyamine, propoxyamine, isopropoxyamine, butoxyamine and the like.

In the above reaction the preferred reactants are benzimidazole compounds (II) bearing $R_3$ substituents which are chemically inert to the sulfonyl chloride reactant. The benzimidazole compound and the sulfonyl chloride are normally employed in approximately equimolar quantities, although an excess of either can be used if desired without adverse effects on the yield of product. The reaction can be carried out in any number of unreactive solvents, including acetone, dimethoxyethane(glyme, DME), tetrahydrofuran (THF), tertiary amides such as N,N-dimethylformamide (DMF), and chlorinated hydrocarbons such dichloromethane, dichloroethane and chloroform. The reaction medium may also contain added base to serve as an acid-binding agent. Some examples of suitable bases for this purpose are pyridine, triethylamine, N-methylmorpholine, sodium bicabonate, and sodium hydride. A preferred solvent medium for the reaction is acetone containing triethylamine or tetrahydrofuran with DMF containing sodium hydroxide as a base.

The reaction is best carried out at a temperature between room temperature and the reflux temperature of the solvent system employed. Preferably, the reaction is carried out at reflux temperature, and at this temperature, the reaction is substantially complete within 1 to 48 hours.

The product of the reaction is a 1-sulfonylbenzimidazole compound, hereinafter called the sulfonylbenzimidazole compound. The product may be isolated by filtering the reaction mixture and concentrating the filtrate to induce crystallization. Alternatively, the reaction mixture can be evaporated to dryness nd the residue treated with a suitable solvent such as acetone or methanol to separate and remove any insoluble material. The solution containing the sulfonylbenzimidazole compound is concentrated to crystallize the product or it is evaporated to give a second residue, which is dissolved in methanol for example. The sulfonylbenzimidazole compound is recovered from the methanol by crystallization.

The reaction of the tautomeric benzimidazole compound and the sulfonyl chloride generally provides a 1:1 mixture of 5-and 6-substituted sulfonylbenzimidazole isomers. The isomers are separable by fractional crystallization or by column chromatography. Usually the 6-isomer crystallizes first from a solution of the mixture. For example, when ethyl 2-amino-5-benzimidazolecarboxylate is reacted with dimethylsulfamoyl chloride in acetone containing triethylamine, ethyl 1-dimethylaminosulfonyl-2-amino-6-benzimidazolecarboxylate crystallizes first from the reaction mixture. The acetone mother liquors contain predominantly ethyl 1-dimethylminosulfonyl-2-amino-5-benzimidazolecarboxylate and residual amounts of the 6-isomer. The isomers can be identified by their nuclear magnetic resonance spectra in the phenyl proton region (7.0 to 8.3 ppm).

Some of the compounds of the invention can be prepared by performing chemical operations such as acetylation, hydrolysis or reduction on the corresponding sulfonylbenzimidazole precursor. When the reactions are performed on a precursor which is an isomeric mixture of sulfonylbenzimidazoles, the isomeric products can be separated by methods such as fractional cystallization or chromatography.

The 2-formamdio, 2-acetamido or 2-propionamido sulfonylebnzimidazoles can be prepared preferably by acylating the corresponding 2-amino sulfonylbenzmidazole (Formula I, $R_2$ is hydrogen) with the anhydride of acetic or propionic acid or the mixed anhydride of formic and acetic acids. For example, a mixture of ethyl 1-dimethylaminosulfonyl-2-amino-5(6)-benzimidazolecarboxylate isomers is stirred with acetic anhydride at room temperature to provide ethyl 1-dimethylaminosulfonyl-2-acetamido-5(6)-benzimidezolecarborylate as a mixture. The isomeric 2-acetamido sulfonylbenzimidazoles can be separated by fractional crystallization from acetone, or preferably, methanol or ethanol.

Mixtures of isomeric sulfonylbenzimidazole ester compounds can be separated by selective hydrolysis of the more labile ester groups. For example, a mixture of ethyl 1-diethylaminosulfonyl-2-amino-5(6)-benzimidazolecarboxylate isomers can be hydrolyzed in aqueous potassium hydroxide. The insoluble unreacted 6-isomer is separated by filtration. The basic aqueous filtrate contains predominantly potassium 1-diethylaminosulfonyl-2-amino-5-benzimidazolecarboxylate and a small amount of the 6-isomer salt. The filtrate is neutralized with dilute acid whereupon 1-diethylaminosulfonyl-2-amino-5-benzimidzaolecarboxylic acid precipitates and is recovered. Ester hydrolysates bearing amino groups in the 2-position should be precipitated in the pH range 5.0 to 7.0.

The sulfonylbenzimidazole carboxylic acid compounds can be reconverted to the esters of primary or secondary alcohols by reaction with thionyl chloride in the presence of such carbinol as are used as the reaction medium. Esters other than the esters of tertiary carbinols can also be prepared from the corresponding 5(6)-sufonylbenzimidazolecarboxylic acids by reaction with molar equivalents of a primary or secondary $C_1$-$C_8$ alkyl carbinol, a $C_3$-$C_7$ sulfoxylbenzyimidazolecarboxamide cycloalkyl alcohol, a $C_3$-$C_7$ cycloalkylmethanol, a 1-($C_3$-$C_7$ cycloalkyl)ethanol, allyl alcohol, propargyl alcohol, benzyl alcohol, α-methylbenzyl alcohol or phenol and 1,1'-carbonyldiimidazole in the presence of a trace of carbinol anion. Preferred esters can be prepared by reacting the appropriate sulfonylbenzimidazolecarboxylic acid with propanol, isopropanol, t-butyl alcohol, neopentyl alcohol, cyclobutanol, cyclohexanol or 1-(cyclopropyl)ethanol (α-methylcyclopropylmethanol) in the presence of 1,1'-carbonyldiimidzole as described above. The sulfonylbenzimidazolecarboxylic acids required are available from the corresponding ethyl ester precursors by basic hydrolysis. Similarly, the N-substituted sulfoxylbenzymidazolecarboxamide compounds can be prepared by reacting the same sulfonylbenzyimidazole-carboxylic acids with a molar equivalent of a $C_1$-$C_4$alkylamine or a $C_1$-$C_4$ alkoxyamine and 1,1'-carbonyldiimidazole in dimethylformamide. When the corresponding 2-acetamido sulfonylbenzimidazolecarboxylic acid is employed as a reactant, the 2-amino ester or amide product can be obtained by basic hydrolysis of the 2-acetyl group after esterification or amidation. For example, when 1-dimethylaminosulfonyl-2-acetamido-5(6)-benzimidazolecarboxylic acid is reacted with one equivalent of isopropylamine or methoxyamine and 1,1'-carbonyldiimidazole in dimethylformamide, the products are respectively 1-dimethylaminosulfonyl-2-amino-5 (6)-N-isopropylbenzimidazolecarboxamide or 1-dimethylaminosulfonyl-2-amino-5(6)-N-methoxybenzimidazolecarboxamide. Primary amides can be obtained when a 5(6)-sulfonylbenzimidazolecarboxylic acid is reacted with ammonia and 1,1'-carbonyldiimidazole.

Preferably, the sulfonyl benzimidazole compounds of Formula I wherein $R_3$ is an ester or amide group are prepared by reacting a benzimidazole compound (Formula II wherein $R_3$ is an amide or ester group) with a sulfonyl chloride $R_1SO_2Cl$ as described previously.

To prepare compounds in which $R^3$ is hydrazinocarbonyl, the ethyl esters of the sulfonylbenzimidazolecarboxylic acids or isomeric mixtures thereof can be reacted with hydrazine in a carbinol solvent to yield the corresponding hydrazides. For example, ethyl 1-dimethylaminosulfonyl-2-amino-5(6)-benzimidazolecarboxylate can be refluxed with hydrazine hydrate in methanol to provide 1-dimethylaminosulfonyl-2-amino-5-(6acid hydrazide. The hydrazide compounds or isomeric mixtures thereof are useful for preparing the corresponding sulfonylbenzimidazolecarboxamide compounds by cleavage of the hydrazide function with Raney nickel. 1-Dimethylaminosulfonyl-2-amino-5(6)-benzimidazolecarboxylic acid hydrazide can be refluxed with Raney nickel in ethanol to provide 1-dimethylaminosulfonyl-2-amino-5(6)-benzimidazolecarboxamide. Amide mixtures are separated by fractional crystallization.

The 5(6)-hydroxymethyl sulfonylbenzimidazole compounds (Formula I, $R_3$ is -$CH_2OH$) can be prepared in several ways. The ethyl esters of the 1-sulfonyl-2-substituted-5(6)-benzimidazolecarboxylic acids can be reduced chemically to provide the corresponding hydroxymethyl compounds. For example, ethyl 1-dimethylaminosulfonyl-2-acetamido-5(6)-benzimidazolecarboxylate can be reduced with sodium bis(2-methoxyethoxy)-aluminum hydride in tetrahydrofuran to provide 1-dimethylaminosulfonyl-2-acetamido-5(6)-hydroxymethylbenzimidazole. A superior method reacts the sulfonyl chloride, $R_1SO_2$ CL, with the appropriate 2-substituted-5 (6)-hydroxymethylbenzimidazole. The required 5(6)-hydroxymethylbenzimidazole reactant can be prepared from the corresponding ethyl 2-substituted-5(6)-benzimidazolecarboxylic acid by reduction with sodium bis(2-methoxyethoxy)-aluminum hydride in an aprotic solvent as described above. The preferred method for preparing large quantities of the hydroxymethyl sulfonyl benzimidazole intermediates begins with 4-chloro-3-nitrobenzyl alcohol. The benzyl alcohol is ammoniated to give 4-amino-3-nitrobenzyl alcohol. The nitro alcohol is hydrogenated catalytically to give 4-hydroxymethyl-o-phenylenediamine. The phenylenediamine is then ring closed to provide the desired 2-substituted-5(6)-hydroxymethylbenzimidazole intermediate by cyclization methods known to the benzimidazole art.

Generally, the sulfonylbenzimidazole carboxylic acid compounds and their hydrazides are useful only as intermediates which can be converted to the corresponding ester or carboxamide compounds. However, some have utility an antiviral agents; e.g., 1-dimethylaminosulfonyl-2-amino-6-benzimidazolecarboxylic acid inhibits Polio I virus at 100 mcg./mg. (see Table I).

The required benzimidazole ester reactants (Formula II wherein $R_3$ is an ester group) can be prepared from the appropriate o-phenylenediamine esters by methods known to the benzimidazole art. For example, 3,4-dinitrobenzoic acid can be reacted with oxalyl chloride and pyridine in benzene to provide the corresponding 3,4-dinitrobenzoyl chloride. This acid chloride is reacted with an appropriate carbinol; i.e., a straight or branched chain alphatic alcohol of one to eight carbon atoms, allyl alcohol, propargyl alcohol, a $C_3$-$C_7$ cycloalkyl alcohol, a ($C_3$-$C_7$ cycloalkyl)methanol, a 1-($C_3$-$C_7$ cycloalkyl)ethanol, benzyl alcohol, α-methylbenzyl alcohol or phenol, in benzene with an acid scavenger such as pyridine to provide the corresponding ester. The appropriate 3,4-dinitrobenzoic acid ester is then hydrogenated at 60 psi in the presence of a catalyst such as Raney nickel or palladium-on-carbon to provide the corresponding o-phenylenediamine ester. Cyclization of an o-phenylendlamine ester thus obtained with cyanogen bromide yields the 2-aminobenzimidazole esters (II where $R^3$ is an ester group).

An alternative method for the preparation of o-phenylenediamine esters beings with 3-nitro-4-chlorobenzoic acid instead of 3,4-dinitrobenzoic acid. Reaction of 3-nitro-4-chlorobenzoic acid as above with oxalyl chloride and pyridifne yields 3-nitro-4-chlorobenzyl chloride. The appropriate 3-nitro-4-chlorobenzoic acid ester is then prepared from the acid chloride as previously described. The 3-nitro-4-chlorobenzoic acid ester is next reacted with dibenzylamine in dimethylformamide at elevated temperatures to give the corresponding 3-nitro-4-dibenzylaminobenzoic acid ester. At this point the nitro dibenzyl ester is hydrogenated catalytically with Raney nickel for example, with concomitant debenzylation and reduction of the nitro group to provide the corresponding o-phenylenediamine ester. As before, the o-phenylenediamine ester is cyclized by methods known to the benzimidazole art to provide the required benzimidazole ester reactants.

The required benzimidazole reactants represented by Formula II, wherein $R_3$ is an amide group, can be prepared from the appropriate o-phenylenediamine amides by known cyclization methods as described above. The o-phenylenediamine amides can be prepared by reacting 3,4-dinitrobenzoyl chloride or 3-nitro-4-chlorobenzoyl chloride described above with a molar equivalent of a $C_1$-$C_4$ alkylamine or a $C_1$-$C_4$ alkoxyamine in the presence of an acid scavenger in an inert solvent. The resulting N-alkoxy or N-alkyl amides of 3,4-dinitrobenzoic acid can be hydrogenated catalytically to provide the corresponding carboxamido o-phenylenediamines. The N-alkoxy or N-alkyl amides of 3-nitro-4-chlorobenzoic acid can be reacted with dibenzylamine in dimethylformamide at elevated temperatures to give the corresponding 3-nitro-4-dibenzylaminobenzoic acid amides. The nitro dibenzyl esters can then be hydrogenated catalytically with Raney nickel for example, with concomitant debenzylation and reduction of the nitro group to provide the corresponding o-phenylenediamine amides. The preparation of a variety of benzimidazoles from o-phenylenediamines is well documented in Weissberger's *The Chemistry of Heterocyclic Compounds, Imidazole and Its Derivatives* (Interscience Publisher Co., New York, 1953).

Other phenylenediamines useful to prepare the required starting materials of Formula II are prepared as follows:

3-Nitro-4-chlorobenzotrifluoride can be ammoniated and reduced to provide 3,4-diaminobenzotrifluoride.

2-(3,4-Diaminophenyl)acetic acid can be prepared by acetylation of 2-(4-aminophenylacetonitrile with acetic anhydride in pyridine. The 2-(4-acetamidophenyl)acetonitrile product is nitrated in acetic anhydride to provide 2-(3-nitrile-4-acetamidophenyl)acetonitrile. The nitrile is hydrolyzed with concentrated hydrochloric acid to give 2-(3-nitro-4-aminophenyl)acetic acid after neutralization. The nitro acid is then hydrogenated at 60 psi at room temperature over palladium-on-carbon to yield 2-(3,4-diaminophenyl)acetic acid. The acid can be esterified with $C_1$-$C_8$ carbinols in the presence of acid catalysts to yield starting materials according to II in which $R^3$ is an ester group. Similarly, the preparation of 2-(3,4-diaminophenyl)propionic acid begins with 2-(4-aminophenyl)-propionitrile as described above for the preparation of the diaminophenylacetic acid.

4-Cyano-o-phenylenediamine can be prepared from 4-aminobenzonitrile by (a) acetylation to provide 4-acetamidobenzonitrile, (b) nitration to yield 3-nitro-4-acetamidobenzonitrile, (c) cleavage of the acetyl group with $PCl_5$ in pyridine to give 3-nitro-4-aminobenzonitrile and (d) hydrogenation of the nitro group at 60 psi with Raney nickel to provide 3,4-diaminobenzonitrile(4-cyano-o-phenylenediamine).

4-Methylsulfonyl-o-phenylenediamine can be prepared by nitrating (4-chlorophenyl) methyl sulfone to yield (3-nitro-4-chlorophenyl) methyl sulfone. The chloro group is ammoniated to give (3-nitro-4-aminophenyl) methyl sulfone. The nitro sulfone can then be hydrogenated with Ruthenium-on-carbon to provide 4-methyllsulfonyl-o-phenylenediamine.

The required benzimidazole reactant (II) are prepared by cyclizing the appropriate o-phenylenediamine compounds with cyanogen bromide as described by Buttle, et al., *Bio Chem. J.* 32, 1101 (1938) and British Patent 551,524. Ethyl 2-amino-5-benzimidazolecarboxylate is described by Paget, et al, *J. Med. Chem.*, 12, 1010 (1969). Illustrative of such benzimidazole compounds which can be reacted with the appropriate sulfonyl chlorides are the 2-aminobenzimidazole reactants (II) which are substituted in the 5(6) position by $C_1$-$C_8$ alkoxycarbonyl, allyloxycarbonyl, propargyloxycarbonyl, ($C_3$-$C_7$ cycloalkyl)oxycarbonyl, ($C_3$-$C_7$ cycloalkyl)methyloxycarbonyl, 1-($C_3$-$C_7$ cycloalkyl)ethyloxycarbonyl, benzyloxycarbonyl, α-methyloxycarbonyl, phenoxycarbonyl, $C_1$-$C_8$ alkoxycarbonylmethyl, 1-($C_1$-$C_8$ alkoxycarbonyl)ethyl, carboxamido, cyano, methylsulfonyl, trifluoromethyl, and the like.

Among the sulfonyl chloride compounds which are required to react with the starting materials of Formula II to prepare the compounds of this invention (I), methanesulfonyl chloride (mesylchloride), isopropylsulfonyl chloride, dimethylsulfamoyl chloride, benzenesulfonyl chloride, 2-thiophenesulfonyl chloride, and 2-acetamido-4-methyl-5-thiazolesulfonyl chloride are commercially available. The preparation of 3-thiophenesulfonyl chloride and 2 (or 3)-furansulfonyl chloride is described by Arcoria et al. [see J. org. Chem., 39 1689 and 3595 (1975)]. 2-Thiazolesulfonyl chloride, 2-thiadiazolesulfonyl chloride, 2-methyl-5-thiadiazolesulfonyl chloride and 2-methylamino-5-thiadiazolesulfonyl chloride are available from 2-thiazolethiol, 2-thiadiazolethiol, 2-methyl-5-thiadiazolethiol and 2-methylamino-5-thiadiazolethiol respectively by oxidation of the thiol function with bromine or chlorine in aqueous solution. Other $C_1$-$C_5$ alkyl and $C_3$-$C_7$ cycloalkyl sulfonyl chlorides can be prepared by the chlorination of the appropriate alkyl thiol or by reacting sulfuryl chloride with sodium alkyl sulfonates derived from the corresponding carbinols and sulfuric acid. The N,N-dialkylsulfamoyl chlorides can be prepared as described by Bindely et al., J. Am. Chem. Soc. 61, 3250 (1939), by reacting the salt of a secondary amine ($R_4R_5NH$) with sulfuryl chloride. Alternatively, they can be prepared by reacting a chloramine compound of the formula $R_4R_5N-Cl$ with a sulfur dioxide at a temperature of −5° to 30° C. The chloramine compounds are prepared by reacting the corresponding secondary amines ($R_4R_5NH$) with antimony pentachloride, sodium hypochlorite or sulfuryl chloride.

Illustrative of other sulfonyl chlorides which can be reacted with the benzimidazole reactants (II) are ethyl-, propyl-, isopropyl-, butyl-, isobutyl- sec-butyl, tert-butyl-, amyl, isoamyl- sec-isoamyl-, and tert-amylsulfonyl chloride.

Yet other sulfamoyl chlorides which can be employed are diethyl-, dipropyl-, N-methyl-N-ethyl-, N-methyl-N-propyl-, N-ethyl-N-propyl-, N-methyl-N-isopropyl-, N-ethyl-N-isopropyl, N-propyl-N-isopropyl-, diisopropyl-, pyrrolidino-, piperidino-, and morpholinosulfamoyl chloride.

For consistency in nomenclature, the sulfonylbenzimidazole compounds will be named as sulfonyl derivatives. For example, the product of the reaction of dimethylsulfamoyl chloride and ethyl 2-amino-5-benzimidazolecarboxylate is named ethyl 1-dimethylaminosulfonyl-2-amino-5(6)benzimidazolecarboxylate rather than ethyl 1-dimethylsulfamoyl-2-amino-5(6)-benzimidazolecarboxylate. The compounds of the invention were tested by the following methods.

TEST METHODS

African green monkey kidney cells (BSC-1) or Hela cells (5-3) were grown in 25 cc. Falcon flasks at 37° C. in medium 199 with 5 percent inactivated fetal bovine serum (FBS), penicillin (150 units 1 ml.) and streptomycin (150 mcg./ml.). When confluent monolayers were formed, the supernatant growth medium was removed and 0.3 ml. of an appropriate dilution of virus (echo, Mengo, Coxsackie, polio or rhinovirus) was added to each flask. After adsorption for one hour at room temperature, the virus infected cell sheet was overlaid with a medium comprising one part of 1 percent Ionagar No. 2 and one part double strength medium 199 with FBS, pencillin, and streptomycin which contains drug at concentrations of 100, 50, 25, 12, 6, 3, 0.75 and 0 micrograms per milliliter (mcg./ml.). The flask containing no drug served as the control for the test. The stock solutions of sulfonylbenzimidazole compounds were made up in dimethylsulfoxide at a concentration of $10^4$ mcg./ml. The flasks wee incubated for 72 hours at 37° C. for polio, Coxsackie, echo, and Megno virus and 120 hours at 32° C. for rhinovirus. Plaques were seen in those areas where the virus infected and reproduced in the cells. A solution of 10 percent formalin and 2 percent sodium acetate was added to each flask to inactivate the virus and fix the cell sheet to the surface of the flask. The virus plaques, irrespective of size, were counted after straining the surrounding cell areas with crystal violet. The plaque count was compared to the control count at each drug concentration. The activity of the test compound was expressed as percentage plaque reduction, or percent inhibition. Alternatively, the drug concentration which inhibits plaque formation by 50 percent indicated by the symbol $I_{50}$ can be used as a measure of activity.

Test results are expressed in terms of Polio virus type I inhibition because the virus is easy to grow and consistent test results are obtained. However, the activity of the preferred compounds was confirmed against other virus cultures. For example, ethyl 1-dimethylaminosulfonyl-2-amino-6-benzimidazolecarboxylate at 3.0 mcg./ml. inhibits Coxsackie (A9, A21, B5), echovirus (strains 1–4), Mengo, rhinovirus (25 strains) and Polio (type I, II, III). Test results for various sulfonylbenzimidazole compounds are summarized in Tables I, II and III below.

In Table I, columns 1–3 give the substituent groups which define the particular sulfonylbenzimidazole compound of Formula I. Columns 4–11 give the percentage plaque reduction for the specified drug concentrations.

In Table II, column 1 names the particular ester of 1-dimethylaminosulfonyl-2-amino-5(6)-benzimidazolecarboxylic acid. Columns 2–4 give the drug concentrations of that particular ester which inhibits virus plague formation by 50 percent ($I_{50}$) for Polio I, rhinovirus strain 3, and Coxsackie virus strain A21 respectively.

In Table III, column 1 names the particular ester of 1-dimethylaminosulfonyl-2-cetamido-5(6)-benzimidazole-carboxylic acid. Columns 2–4 give the drug concentration of that particular ester which inhibits virus plaque formation by 50 percent ($I_{50}$) for Polio I, rhinovirus strain 3 and Coxsackie virus strain A21 respectively.

TABLE I

Percent Plaque Reduction (Polio I)

| $R^1$ | $R^2$ | $R^3$ | Drug Concentration (mcg./ml.) | | | | | | | |
|---|---|---|---|---|---|---|---|---|---|---|
| | | | 100 | 50 | 25 | 12 | 6 | 3 | 1.5 | 0.75 |
| | | | Percent Plaque Reduction | | | | | | | |
| $Me_2N$ | H | 6-$CO_2Et$ | | 64 | 0 | 0 | 0 | 0 | | |
| $Me_2N$ | $CH_3$ | 6-$CO_2Et$ | | 90 | 80 | 50 | 22 | 0 | | |
| $Me_2N$ | $NH_2$ | 5-$CO_2Et$ | | | 100 | 98 | 72 | 37 | 25 | 0 |
| $Me_2N$ | $NH_2$ | 6-$CO_2Et$ | | 100 | 100 | 100 | 100 | 100 | 96 | 52 |
| methyl | $NH_2$ | 6-$CO_2Et$ | | | | 87 | 51 | 24 | 0 | 0 |
| isopropyl | $NH_2$ | 6-$CO_2Et$ | | | | 100 | 100 | 98 | 54 | 24 |
| $Me_2N$ | $NH_2$ | 5-$CF_3$ | 62 | 64 | 64 | 61 | 51 | 0 | | |
| pyrrolidino | $NH_2$ | 5(6)-$CO_2Et$* | | 100 | 100 | 100 | 99 | 63 | | |
| piperidino | $NH_2$ | 5(6)-$CO_2Et$* | | toxic | toxic | 100 | 100 | 3 | | |
| morpholino | $NH_2$ | 5(6)-$CO_2Et$* | | 100 | 99 | 86 | 3 | 0 | | |
| $Me_2N$ | $NH_2$ | 6-$CO_2Me$ | | | | | 100 | 97 | 60 | 35 |
| $Me_2N$ | $NH_2$ | 6-$CO_2C_4H_9$ | | | | | 100 | 98 | 63 | 28 |
| Me(Et)N | $NH_2$ | 6-$CO_2Et$ | | | | 100 | 100 | 100 | 83 | 51 |
| Me(Pr)N | $NH_2$ | 6-$CO_2Et$ | | | | 100 | 100 | 90 | 52 | 35 |
| $Et_2N$ | $NH_2$ | 6-$CO_2Et$ | | | | 100 | 100 | 87 | 43 | 25 |
| $Me_2N$ | $NH_2$ | 6-COOH | 50 | | 34 | | 23 | 17 | | |
| $Me_2N$ | $NH_2$ | 5-$CONH_2$ | 55 | 32 | 30 | 25 | 23 | 8 | | |
| $Me_2N$ | $NH_2$ | 6-$CONH_2$ | 100 | 100 | 100 | 78 | 43 | 36 | 27 | |
| $Me_2N$ | $NH_2$ | 5-CONHEt | 97 | 54 | 21 | 7 | | | | |
| $Me_2N$ | $NH_2$ | 6-CONHEt | 100 | 100 | 100 | 99 | 80 | 40 | 9 | |

*Isomeric mixtures

The drug concentration of various esters other than the ethyl esters which inhibit virus plaque formation by 50 percent ($I_{50}$) are summarized in Tables II and III

TABLE II

Virus Inhibition ($I_{50}$) of Esters of 1-Dimethylaminosulfonyl-2-Amino-5(6)-Benzimidazolecarboxylic Acids

| Ester* | $I_{50}$ (mcg/ml) | | |
|---|---|---|---|
| | Polio I | Rhino 3 | Cox A21 |
| (6)methyl | 3 | 0.75 | 3 |
| propyl | 1.5 | 3 | 1.5 |
| (6)-isopropyl | 0.35 | 0.75 | 1.5 |
| allyl | 3–6 | | |
| propargyl | 3–6 | | |

TABLE II-continued

Virus Inhibition ($I_{50}$) of
Esters of 1-Dimethylaminosulfonyl-2-
Amino-5(6)-Benzimidazolecarboxylic Acids

| Ester* | $I_{50}$ (mcg/ml) | | |
|---|---|---|---|
| | Polio I | Rhino 3 | Cox A21 |
| butyl | 3 | 0.75 | 3 |
| (5)-isobutyl | 3 | 3–6 | 3 |
| (6)-neopentyl | 0.75 | 0.75 | 1.5 |
| (5)-neopentyl | 3 | | |
| octyl | 50 | | |
| (6)cyclohexyl | 0.35 | 1.5 | 0.75 |
| cyclohexylmethyl | 3–6 | 1.5 | |
| benzyl | 6 | | |
| α-methylbenzyl | 3 | | |

*The isomer is indicated by number; otherwise the ester is an isomeric mixture. mcg/ml is the drug concentration in micrograms per milliliter.

TABLE III

Virus Inhibition ($I_{50}$) of
Esters of 1-Dimethylaminosulfonyl-2-Acetamido-
5(6)-Benzimidazolecarboxylic Acid

| Ester* | $I_{50}$ (mcg/ml) | | |
|---|---|---|---|
| | Polio I | Rhino 3 | Cox A21 |
| isopropyl | 0.75 | | |
| (5)-isobutyl | 3 | | |
| (6)-isobutyl | 0.75 | <3 | 0.75–1.5 |
| neopentyl | 1.5–3 | | |
| sec-butyl | 0.75 | | |
| (5)-cyclopropylmethyl | 6 | | |
| (6)-cyclopropylmethyl | 0.75–1.5 | | 1.5 |
| cyclohexylmethyl | 3 | | 1.5–3 |
| 3-methylcyclohexylmethyl | 3 | | |
| 1-(cyclopropyl)ethyl | 0.75 | <5 | 1.5 |
| cyclobutyl | 0.35 | <5 | 1.5 |
| cyclohexyl | 1.5 | | |
| (6)-phenyl | 3–6 | | |

*The isomer is indicated by number otherwise the ester is an isomeric mixture. mcg/ml is the drug concentration in micrograms per milliliter.

The sulfonylbenzimidazole compounds were tested as pure compounds and as isomer mixtures. Both isomers inhibit virus growth, the 6-isomer generally being more active than the 5-isomer. For example, ethyl 1-dimethylaminosulfonyl-2-amino-6-benzimidazolecarboxylate inhibited Polio I virus completely at a concentration as low as 3.0 mcg./ml. The 5-isomer inhibited completely at a concentration of 12.0 mcg.ml.

Among the preferred compounds of the invention are the 1-($C_1$-$C_5$)alkylsulfonyl-2-amino-5(6)-benzimidazolecarboxylate esters. Especially preferred are the 1-(aminosulfonyl)-2-amino-5-(6)-benzimidazolecarboxylate esters. Most preferred are the ethyl, propyl, isopropyl, t-butyl, neopentyl, cyclobutyl, cyclohexyl and 1-(cycloprpyl)ethyl esters of the 1-(N,N-dialkylaminosulfonyl)-25(6)-benzimidazolecarboxylic acids. The 6-isomers are preferred over 5-isomers.

Classes of compounds coming within the scope of this invention are those wherein $R_1$ is $R_4R_5N$- and $R_4$ and $R_5$ are $C_1$-$C_3$ alkyl, $R_2$ is hydrogen and $R_3$ is an oxycarbonyl group selected from $C_1$-$C_8$ alkoxycarbonyl, allyloxycarbonyl, proparglyxoycarbonyl, ($C_3$-$C_7$ cycloalkyl)oxycarbonyl, ($C_3$-$C_7$ cycloalkyl)methyloxycarbonyl, 1-($C_3$-$C_7$ cycloalkyl)ethyloxycarbonyl, benzyloxycarbonyl, α-methylbenzyloxycarbonyl or phenoxycarbonyl.

Compounds coming within the scope of the above formula are able to suppress the growth of certain viruses when added to a medium in which the virus is growing. The compounds of the invention can therefore be used in aqueous solution, preferably with a surfactant, to decontaminate surfaces on which polio, Coxsackie, rhinovirus and other viruses are present, such surfaces including hospital glassware, hospital working surfaces and similar areas in the preparation of food.

Furthermore, the compounds can be orally administered to warm-blooded animals and humans in a dose of 1 to 300 mg./kg. of animal body weight. The administration can be repeated periodically as needed. In accordance with general practice, the antiviral compound can be administered every 4 to 6 hours.

Preferably, the compounds to be employed in accordance with the present invention are employed in combination with one or more adjuvants suited to the particular route of administration. Thus, in the case of oral administration, the compound is modified with pharmaceutical diluents or carriers such as lactose, sucrose, starch powder, cellulose, talc, magnesium stearate, magnesium oxide, calcium sulfate, acacia powder, gelatin, sodium alginate, sodium benzoate and stearic acid. Such compositions can be formulated as tablets or enclosed in capsules for convenient administration. In addition, the compounds can be administered parenterally.

The compounds can also be mixed with a liquid and administered as nose drops or intranasal spray.

Illustrative of the esters and amides of the sulfonylbenzimidazolecarboxylic acid compounds provided by this invention are the following:

1-Cyclopropylsulfonyl-2-formamido-5(6)-benzimidazolecarboxylic acid, cyclopropyl ester, 1-(2-Furan)sulfonyl-2-amino-5(6)-benzimidazolecarboxylic acid, cyclopentyl ester, 1-(2-Thiophene)sulfonyl-2-propionamido-5(6)-benzimidazolecarboxylic acid, cyclohexyl ester, 1-(2-Thiazole)sulfonyl-2-acetamido-5(6)-benzimidazolecarboxylic acid, cycloheptyl ester, 1-(2-Thiazole)sulfonyl-2-acetamido-5(6)-benzimidazolecarboxylic acid, cycloheptyl ester, 1-Cyclopentylsulfonyl-2-amino-5(6)-benzimidazolecarboxylic acid, cyclopropylmethyl ester, 1-[2-(1,3,4-thiadiazole)sulfonyl]-2-amino-5(6)-benzimidazolecarboxylic acid, cyclobutylmethyl ester, 1-Cyclohexylsulfonyl-2-formamido-5(6)-benzimidazolecarboxylic acid, cyclopentylmethyl ester, 1-Isopropylsulfonyl-2-amino-5(6)-benzimidazolecarboxylic acid, cycloheptylmethyl ester, 1-Dimethylaminosulfonyl-2-amino-5(6)-benzimidazolecarboxylic acid, 1-(cyclopropyl)ethyl ester, 1-Piperidinosulfonyl-2-acetamido-5(6)-benzimidazolecarboxylic acid, 1-(cyclobutyl)ethyl ester, 1-Pyrrolidinosulfonyl-2-amino-5(6)-benzimidazolecarboxylic acid, 1-(cyclopentyl)ethyl ester, 1-Diethylaminosulfonyl-2-formamido-5(6)-benzimidazolecarboxylic acid, 1-(cyclohexyl)ethyl ester, 1-Dipropylaminosulfonyl-2-formamido-5(6)-benzimidazolecarboxylic acid, 1-(cycloheptyl)ethyl ester, 1-Dimethylaminosulfonyl-2-amino-5(6)-benzimidazolecarboxylic acid, 2-methylcyclohexyl ester, 1-Diethylaminosulfonyl-2-amino-5(6)-benzimidazolecarboxylic acid, 3-methylcyclohexyl ester, Isopropyl 1-(2-furan)sulfonyl-2-acetamido-5(6)-benzimidazolecarboxylate, Neopentyl 1-(2-thiazole)sulfonyl-2-amino-5(6)-benzimidazolecarboxylate, Cyclohexyl 1-(2-acetamido-4-methylthiazol-5-yl)sulfonyl-2-propionamido-5(6)-benzimidazolecarboxylate,
1-(2-Methylamino-1,3,4-thiadiazol-5-yl)sulfonyl-2-formamido-5(6)-benzimidazolecarboxylic acid, 1-(cyclopropyl)ethyl ester,
Neopentyl 1-dimethylaminosulfonyl-2-acetamido-5(6)-benzimidazolecarboxylate,
Isopropyl 1-isopropylsulfonyl-2-amino-5(6)-benzimidazolecarboxylate,
Neopentyl 1-benzenesulfonyl-2-formamido-5(6)-benzimidazolecarboxylate,
Cyclobutyl 1-(2-thiophene)sulfonyl-2-propionamido-5(6)-benzimidazolecarboxylate,
Cyclohexyl 1-(2-thiazole)sulfonyl-2-amino-5(6)-benzimidazolecarboxylate,
1-Dimethylaminosulfonyl-2-amino-5(6)-benzimidazolecarboxylic acid, 1-(cyclopropyl)ethyl ester,
Neopentyl 1-dimethylaminosulfonyl-2-amino-5(6)-benzimidazolecarboxylate,
Cyclobutyl 1-(N-methyl-N-ethylaminosulfonyl)-2-amino-5(6)-benzimidazolecarboxylate,
Isopropyl 1-(N-methyl-N-propylaminosulfonyl)-2-acetamido-5(6)-benzimidazolecarboxylate,
Cyclohexyl 1-dipropylaminosulfonyl-2-formamido-5(6)-benzimidazolecarboxylate,
Isopropyl 1-pyrrolidinosulfonyl-2-amino-5(6)-benzimidazolecarboxylate,
Neopentyl 1-piperidinosulfonyl-2-acetamido-5(6)-benzimidazolecarboxylate,
Cyclobutyl 1-piperidinosulfonyl-2-propionamido-5(6)-benzimidazolecarboxylate,
1-Isopropylsulfonyl-2-acetamido-5(6)-benzimidazolecarboxylic acid, 4-methylcyclohexyl ester,
1-Dimethylaminosulfonyl-2-amino-5(6)-benzimidazolecarboxylic acid, 1-methylcyclohexyl ester,
1-Dimethylaminosulfonyl-2-acetamido-5(6)-N-methylbenzimidazolecarboxamide,
1-(2-Methyl-1,3,4-thiadiazol-5-yl)sulfonyl-2-formamido-5(6)-N-ethylbenzimidazolecarboxamide,
1-Pyrrolidinosulfonyl-2-propionamido-5(6)-N-propylbenzimidazolecarboxamide,
1-Morpholinosulfonyl-2-acetamido-5(6)-N-isopropylbenzimidazolecarboxamide,
1-Dipropylaminosulfonyl-2-amino-5(6)-N-butylbenzimidazolecarboxyamide,
1-[(3-Furan)sulfonyl]-2-formamido-5(6)-N-sec-butylbenzimidazolecarboxamide,
1-Pyrrolidinosulfonyl-2-propionamido-5(6)-N-isobutylbenzimidazolecarboxamide,
1-Phenylsulfonyl-2-amino-5(6)-N-tert-butylbenzimidazolecarboxamide,
1-Butylsulfonyl-2-acetamido-5(6)-N-methoxybenzimidazolecarboxamide,
1-Isobutylsulfonyl-2-formamido-5(6)-N-ethoxybenzimidazolecarboxamide,
1-Diisopropylaminosulfonyl-2-propionamido-5(6)-N-propoxybenzimidazolecarboxamide,
1-Diethylaminosulfonyl-2-acetamido-5(6)-N-isopropoxybenzimidazolecarboxamide,
1-Dimethylaminosulfonyl-2-amino-5(6)-N-butoxybenzimidazolecarboxamide, cyclobutyl 1-dimethylaminosulfonyl-2-amino-5(6)-benzimidazolecarboxylate,
1-Piperidinosulfonyl-2-amino-5(6)-N-isobutoxybenzimidazolecarboxamide,
1-[(5-Methyl-1,3,4-thiadiazol-5-yl)sulfonyl]-2-formamido-5(6)-N-sec-butoxybenzimidazolecarboxamide, and
1-Cyclopropylsulfonyl-2-acetamido-5(6)-N-tert-butoxybenzimidazolecarboxamide.

Further illustrative of the sulfonylbenzimidazole compounds provided by this invention are the following:
1-methylsulfonyl-2-amino-5(6)-cyanobenzimidazole,
1-ethylsulfonyl-2-amino-5(6)-methylsulfonylbenzimidazole,
1-propylsulfonyl-2-amino-5(6)-trifluoromethylbenzimidazole,
1-isopropylsulfonyl-2-formamido-5(6)-methylsulfonylbenzimidazole,
1-butylsulfonyl-2-propionamido-5(6)-trifluoromethylbenzimidazole,
1-isobutylsulfonyl-2-amino-5(6)-hydroxymethylbenzimidazole,
1-(sec-butylsulfonyl)-2-amino-5(6)-benzimidazolecarboxamide,
1-(tert-butylsulfonyl)-2-formamido-5(6)-benzimidazolecarboxylic acid hydrazide,
neopentyl 1-cyclopentylsulfonyl-2-acetamido-5(6)-benzimidazolecarboxylate,
1-morpholinosulfonyl-2-amino-5(6)-N-propylbenzimidazolecarboxamide,
propargyl 1-piperidinosulfonyl-2-propionamido-5(6)-benzimidazolecarboxylate,
1-(2-methylamino-1,3,4-thiadiazol-5-yl)sulfonyl-2-amino-5(6)-N-methoxybenzimidazolecarboxamide,
1-dipropylaminosulfonyl-2-acetamido-5(6)-N-ethylbenzimidazolecarboxamide,
1-(2-methyl-1,3,4-thiadiazol-5-yl)sulfonyl-2-amino-5(6)-benzimidazolecarboxylic acid, α-methylbenzyl ester,
1-(N-methyl-N-propylaminosulfonyl)-2-amino-5(6)-N-isopropoxybenzimidazolecarboxamido,
1-(2-thiophene)sulfonyl-2-acetamido-5(6)-hydroxymethylbenzimidazole,
1-(2-acetamido-4-methylthiazol-5-yl)sulfonyl-2-formamido-5(6)-hydroxymethylbenzimidazole,
1-piperidinosulfonyl-2-acetamido-5(6)-hydroxymethylbenzimidazole,
1-(N-methyl-N-propylaminosulfonyl)-2-amino-5(6)-hydroxymethylbenzimidazole,
neopentyl 1-isopropylsulfonyl-2-propionamido-5(6)-benzimidazolecarboxylate,
propargyl 1-cyclohexylsulfonyl-2-amino-5(6)-benzimidazolecarboxylate,
1-(N-methyl-N-ethylaminosulfonyl)-2-amino-5(6)-benzimidazolecarboxylic acid, phenyl ester,
1-cyclopropylsulfonyl-2-formamido-5(6)-benzimidazolecarboxylic acid, phenyl ester,
1-piperidinosulfonyl-2-acetamido-5(6)-benzimidazolecarboxylic acid, phenyl ester,
1-amylsulfonyl-2-amino-5(6)-benzimidazolecarboxylic acid,
1-isoamylsulfonyl-2-formamido-5(6)-benzimidazole,
1-(sec-isoamylsulfonyl)-2-amino-5(6)-methylsulfonylbenzimidazole,
1-(tert-amylsulfonyl)-2-propionamido-5(6)-trifluoromethylbenzimidazole,
1-(N-methyl-N-ethylaminosulfonyl)-2-amino-5(6)-methylsulfonylbenzimidazole,
1-(N-methyl-N-propylaminosulfonyl)-2-amino-5(6)-trifluoromethylbenzimidazole,
1-(N-methyl-N-isopropylaminosulfonyl)-2-formamido-5(6)-hydroxymethylbenzimidazole, 1-diethylaminosulfonyl-2-amino-5(6)-methylsulfonylbenzimidazole,
1-(N-ethyl-N-propylaminosulfonyl)-2-amino-5(6)-trifluoromethylbenzimidazole,
1-(N-ethyl-N-isopropylaminosulfonyl)-2-amino-5(6)-benzimidazolecarboxamide,
1-dipropylaminosulfonyl-2-formamido-5(6)-benzimidazolecarboxylic acid hydrazide,
1-(N-propyl-N-isopropylaminosulfonyl)-2-acetamido-5(6)-benzimidazolecarboxylic acid,
1-diisopropylaminosulfonyl-2-amino-5(6)-cyanobenzimidazole,
1-benzenesulfonyl-2-amino-5(6)-methylsulfonylbenzimidazole,
1-pyrrolidinosulfonyl-2-formamido-5(6)-trifluoromethylbenzimidazole,
1-benzenesulfonyl-2-amino-5(6)-benzimidazolecarboxylic acid, phenyl ester,
cyclobutyl 1-(2-thiazole)sulfonyl-2-acetamido-5(6)-benzimidazolecarboxylate,
1-(2-acetamido-4-methylthiazol-5-yl)sulfonyl-2-formamido-5(6)-hydroxymethylbenzimidazole,
1-(2-methylamino-1,3,4-thiadiazol-5-yl)sulfonyl-2-amino-5(6)-N-butylbenzimidazolecarboxamide,
1-cyclopropylsulfonyl-2-amino-5(6)-hydroxymethylbenzimidazole,
1-(3-furan)sulfonyl-2-acetamido-5(6)-benzimidazolecarboxylic acid, phenyl ester,
1-(2-acetamido-4-methylthiazol-5-yl)sulfonyl-2-amino-5(6)-benzimidazolecarboxylic acid, 1-(cyclopropyl)ethyl ester,
1-(2-thiophene)sulfonyl-2-acetamido-5(6)-N-butoxybenzimidazolecarboxamide,
1-diethylaminosulfonyl-2-amino-5(6)-N-butylbenzimidazolecarboxamide,
neopentyl 1-cyclohexylsulfonyl-2-acetamido-5(6)-benzimidazolecarboxylate,
allyl 1-(2-methylamino-1,3,4-thiadiazol-5-yl)sulfonyl-2-propionamido-5(6)-benzimidazolecarboxylate,
propargyl 1-(1,3,4-thiadiazol-2-yl)sulfonyl-2-acetamido-5(6)-benzimidazolecarboxylate,
1-(1,3,4-thiadiazol-2-yl)sulfonyl-2-formamido-5(6)-N-propylbenzimidazolecarboxamide,
1-isopropylsulfonyl-2-amino-5(6)-benzimidazolecarboxylic acid, cyclobutylmethyl ester,
1-dimethylaminosulfonyl-2-acetamido-5(6)-benzimidazolecarboxylic acid, 1-(cyclohexyl)ethyl ester,
1-(2-methylamino-1,3,4-thiadiazol-5-yl)sulfonyl-2-acetamido-5(6)-benzimidazolecarboxylic acid, α-methylbenzyl ester, 1-cycloheptylsulfonyl-2-amino-5(6)-benzimidazolecarboxylic acid, 1-(cycloheptyl)ethyl ester,
1-piperidinosulfonyl-2-propionamido-5(6)-hydroxymethylbenzimidazole,
1-morpholinosulfonyl-2-amino-5(6)-methylsulfonylbenzimidazole,
1-methylsulfonyl-2-formamido-5(6)-benzimidazolecarboxylic acid, 2,2,4-trimethyl-1-pentyl ester,
1-ethylsulfonyl-2-amino-5(6)-benzimidazolecarboxylic acid, isooctyl ester,
1-propylsulfonyl-2-amino-5(6)-benzimidazolecarboxylic acid, 2-ethylhexyl ester,
1-isopropylsulfonyl-2-propionamido-5(6)-benzimidazolecarboxylic acid, 2-octyl ester,
1-butylsulfonyl-2-amino-5(6)-benzimidazolecarboxylic acid, 2-heptyl ester,
1-isobutylsulfonyl-2-amino-5(6)-benzimidazolecarboxylic acid, octyl ester,
1-(sec-butylsulfonyl)-2-amino-5(6)-benzimidazolecarboxylic acid, heptyl ester,
1-(tert-butylsulfonyl)-2-formamido-5(6)-benzimidazolecarboxylic acid, heptyl ester,
1-amylsulfonyl-2-propionamido-5(6)-benzimidazolecarboxylic acid, octyl ester,
1-isoamylsulfonyl-2-amino-5(6)-benzimidazolecarboxylic acid, 4-methyl-2-pentyl ester,
1-(1,2-dimethylpropylsulfonyl)-2-amino-5(6)-benzimidazolecarboxylic acid, isooctyl ester,
1-(tert-amylsulfonyl)-2-acetamido-5(6)-benzimidazolecarboxylic acid, propyl ester,
propargyl 1-pyrrolidinosulfonyl-2-acetamido-5(6)-benzimidazolecarboxylate,
cyclobutyl 1-(N-methyl-N-isopropylaminosulfonyl)-2-acetamido-5(6)-benzimidazolecarboxylate,
1-(2-acetamido-4-methylthiazol-5-yl)sulfonyl-2-amino-5(6)-N-isopropylbenzimidazolecarboxamide,
1-(2-thiophene)sulfonyl-2-amino-5(6)-N-isopropoxybenzimidazolecarboxamide,
neopentyl 1-(2-thiazole)sulfonyl-2-formamido-5(6)-benzimidazolecarboxylate,
allyl 1-piperidinosulfonyl-2-propionamido-5(6)-benzimidazolecarboxylate,
neopentyl 1-(2-methylamino-1,3,4-thiadiazol-5-yl)-sulfonyl-2-amino-5(6)-benzimidazolecarboxylate,
1-(N-methyl-N-propylaminosulfonyl)-2-acetamido-5(6)-benzimidazolecarboxylate, 1-(cyclobutyl)ethyl ester,
1-dimethylaminosulfonyl-2-acetamido-51 (6)-benzimidazolecarboxylic acid, phenyl ester,
1-(2-acetamido-4-methylthiazol-5-yl)sulfonyl-2-amino-5(6)-benzimidazolecarboxylic acid, phenyl ester,
1-isopropylsulfonyl-2-amino-5(6)-benzimidazolecarboxylic acid, phenyl ester,
1-cyclopropylsulfonyl-2-acetamido-5(6)-benzimidazolecarboxylic acid, 1-(cyclopropyl)ethyl ester,
propargyl 1-dipropylaminosulfonyl-2-propionamido-5(6)-benzimidazolecarboxylate,
1-(2-furan)sulfonyl-2-acetamido-5(6)-benzimidazolecarboxylic acid, cyclopropylmethyl ester,
1-benzenesulfonyl-2-amino-5(6)-benzimidazolecarboxylic acid, cyclopropylmethyl ester,
cyclobutyl 1-(N-methyl-N-ethylaminosulfonyl)-255(6)-benzimidazolecarboxylate,
1-dimethylaminosulfonyl-2-amino-5(6)-benzimidazolecarboxylic acid, phenyl ester,
1-dimethylaminosulfonyl-2-acetamido-5(6)-benzimidazolecarboxylic acid, 2,2,4-trimethyl-1-pentyl ester,
1-(N-methyl-N-ethylaminosulfonyl)-2-amino-5(6)-benzimidazolecarboxylic acid, isopropyl ester,
1-(N-methyl-N-propylaminosulfonyl)-2-amino-5(6)-benzimidazolecarboxylic acid, butyl ester,
1-(N-methyl-N-isopropylaminosulfonyl)-2-formamido-5(6)-benzimidazolecarboxylic acid, isobutyl ester,
1-diethylaminosulfonyl-2-amino-5(6)-benzimidazolecarboxylic acid, hexyl ester,
1-(N-ethyl-N-propylaminosulfonyl)-2-amino-5(6)-benzimidazolecarboxylic acid, 2-heptyl ester,
1-(N-ethyl-N-isopropylaminosulfonyl)-2-amino-5(6)-benzimidazolecarboxylic acid, methyl ester,
1-dipropylaminosulfonyl-2-acetamido-5(6)-benzimidazolecarboxylic acid, isobutyl ester, 1-(N-propyl-N-isopropylaminosulfonyl)-2-amino-5(6)-benzimidazolecarboxylic acid, propyl ester,
1-diisopropylaminosulfonyl-2-amino-5(6)-benzimidazolecarboxylic acid, 2-ethylhexyl ester,
1-benzenesulfonyl-2-propionamido-5(6)-benzimidazolecarboxylic acid, butyl ester,
1-pyrrolidinosulfonyl-2-acetamido-5(6)-benzimidazolecarboxylic acid, 2-octyl ester,
1-piperidinosulfonyl-2-amino-5(6)-benzimidazolecarboxylic acid, heptyl ester,
1-morpholinosulfonyl-2-amino-5(6)-benzimidazolecarboxylic acid, 2-ethyl-1-butyl ester,
neopentyl 1-(1,3,5-thiadiazol-2-yl)sulfonyl-2-formamido-5(6)-benzimidazolecarboxylate,
1-benzenesulfonyl-2-amino-5(6)-benzimidazolecarboxylic acid, cycloheptylmethyl ester,
neopentyl 1-morpholinosulfonyl-2-acetamido-5(6)-benzimidazolecarboxylate,
cyclohexyl 1-cyclohexylsulfonyl-2-amino-5(6)-benzimidazolecarboxylate,
benzyl 1-(1,3,4-thiadiazol-2-yl)sulfonyl-2-acetamido-5(6)-benzimidazolecarboxylate,
allyl 1-(2-methyl-1,3,4-thiadiazol-5-yl)sulfonyl-2-acetamido-5(6)-benzimidazolecarboxylate,
allyl 1-isopropylsulfonyl-2-amino-5(6)-benzimidazolecarboxylate,
propargyl 1-benzenesulfonyl-2-acetamido-5(6)-benzimidazolecarboxylate,
cyclobutyl 1-(2-acetamido-4-methylthiazol-5-yl)-sulfonyl-2-formamido-5(6)-benzimidazolecarboxylate,
neopentyl 1-(2-methyl-1,3,4-thiadiazol-5-yl)-sulfonyl-2-amino-5(6)-benzimidazolecarboxylate,
1-pyrrolidinosulfonyl-2-acetamido-5(6)-benzimidazolecarboxylic acid, 1-(cyclopropyl)ethyl ester,
benzyl 1-(2-thiophene)sulfonyl-2-acetamido-5(6)-benzimidazolecarboxylate,
propargyl 1-(2-methyl-1,3,4-thiadiazol-5-yl)-sulfonyl-2-amino-5(6)-benzimidazolecarboxylate,
isopropyl 1-(3-furan)sulfonyl-2-acetamido-5(6)-benzimidazolecarboxylate,
1-cyclobutylsulfonyl-2-amino-5(6)-benzimidazolecarboxylic acid, 1-(cyclopropyl)ethyl ester,
cyclobutyl 1-(N-methyl-N-ethylaminosulfonyl)-2-amino-5(6)-benzimidazolecarboxylate,
2-(1-methylsulfonyl-2-H-benzimidazole-5-yl)-acetic acid, 4-methyl-2-pentyl ester.
2-(1-benzenesulfonyl-2-methylbenzimidazol-5-yl)-acetic acid, 2-methyl-1-pentyl ester,
2-(1-dimethylaminosulfonyl-2-acetamidobenzimidazol-5-yl)acetic acid, ethyl ester,
2-(1-morpholinosulfonyl-2-aminobenzimidazol-5-yl)-acetic acid, tert-butyl ester,
2-(1-methylsulfonyl-2-H-benzimidazol-5-yl)propionic acid, methyl ester,
2-(1-benzenesulfonyl-2-aminobenzimidazol-5-yl)-propionic acid, isopropyl ester,
2-(1-dimethylaminosulfonyl-2-acetamidobenzimidazol-5-yl)propionic acid, sec-butyl ester,
2-(1-pyrrolidinosulfonyl-2-methylaminobenzimidazol-5-yl)propionic acid, isooctyl ester,
2-(1-diisopropylaminosulfonyl-2-methylbenzimidazol-5-yl)propionic acid, 2-ethylhexyl ester,
1-methylsulfonyl-2-acetamido-5(6)-cyanobenzimidazole,
1-benzenesulfonyl-2-formamido-5(6)-cyanobenzimidazole,
1-isopropylsulfonyl-2-acetamido-5(6)-cyanobenzimidazole,
1-dimethylaminosulfonyl-2-amino-5(6)-cyanobenzimidazole,
1-pyrrolidinosulfonyl-2-amino-5(6)-hydroxymethylbenzimidazole,
1-(N-ethyl-N-propylaminosulfonyl)-2-acetamido-5(6)-cyanobenzimidazole,
neopentyl 1-(N-methyl-N-propylaminosulfonyl)-2-acetamido-5(6)-benzimidazolecarboxylate,
1-(2-methyl-1,3,4-thiadiazol-5-yl)sulfonyl-2-propionamido-5(6)-benzimidazolecarboxylic acid, α-methylbenzyl ester,
propargyl 1(N-methyl-N-isopropylaminosulfonyl)-2-acetamido-5(6)-benzimidazolecarboxylate,
1-cyclopropylsulfonyl-2-amino-5(6)-benzimidazolecarboxylic acid hydrazide,
1-(2-thiophene)sulfonyl-2-formamido-5(6)-benzimidazolecarboxamide,
1-(N-ethyl-N-propylaminosulfonyl)-2-acetamido-5(6)-benzimidazolecarboxamide,
1-piperidinosulfonyl-2-amino-5(6)-benzimidazolecarboxylic acid hydrazide,
1-benzenesulfonyl-2-acetamido-5(6)-N-ethoxybenzimidazolecarboxamide,
1-dimethylaminosulfonyl-2-amino-5(6)-N-isopropoxybenzimidazolecarboxamide,
1-(2-methyl-1,3,4-thiadiazol-5-yl)sulfonyl-2-amino-5(6)-benzimidazolecarboxylic acid hydrazide,
1-(2-acetamido-4-methylthiazol-5-yl)-2-amino5(6)-benzimidazolecarboxamide,
1-(1,3,4-thiadiazol-2-yl)sulfonyl-2-amino-5(6)-benzimidazolecarboxylic acid hydrazide,
1-dipropylaminosulfonyl-2-amino-5(6)-benzimidazolecarboxylate, phenyl ester,
1-dimethylaminosulfonyl-2-acetamido-5(6)-benzimidazolecarboxylic acid hydrazide,
1-(2-acetamido-4-methylthiazol-5-yl)sulfonyl-2-acetamido-5(6)-benzimidazolecarboxylic acid hydrazide,
1-(1,3,4-thiadiazol-2-yl)sulfonyl-2-formamido-5(6)-benzimidazolecarboxylic acid, 1-(cyclopropyl)ethyl ester,
allyl 1-butylsulfonyl-2-amino-5(6)-benzimidazolecarboxylate,
1-benzenesulfonyl-2-amino-5(6)-cyanobenzimidazole,
1-benzenesulfonyl-2-acetamido-5(6)-hydroxymethylbenzimidazole,
1-benzenesulfonyl-2-acetamido-5(6)-trifluoromethylbenzimidazole,
1-benzenesulfonyl-2-amino-5(6)-hydroxymethylbenzimidazole,
1-dimethylaminosulfonyl-2-acetamido-5(6)-hydroxymethylbenzimidazole,
1-dimethylaminosulfonyl-2-acetamido-5(6)-hydroxymethylbenzimidazole, and
1-dimethylaminosulfonyl-2-acetamido-5(6)-trifluoromethylbenzimidazole.

The following examples further illustrate the preparation of the starting materials, intermediates, and compounds of the invention.

EXAMPLE 1

Ethyl 3,4-Diaminobenzoate

One mole (152 g.) of 3,4-diaminobenzoic acid was stirred with 2 liters of ethanol in a Morton flask. Hydrogen chloride gas was passed through the stirred suspension for about 2 hours. As the gas was absorbed, the slurry became gel-like in character. Ethanol (500 ml.) was added to the reaction mixture to disperse the gel. The reaction mixture was refluxed 24 hours. The mixture was filtered and the filtrate was evaporated to dryness in vacuo. The filter cake and the filtrate residue were dissolved in 9 liters of water. The aqueous solution was made basic by the addition of solid sodium carbonate. The product precipitated from the basic solution. The material was filtered and dried to yield 130 grams of ethyl 3,4-diaminobenzoate.

EXAMPLE 2

Cyclohexyl 2-Amino-5(6)-Benzimidazolecarboxylate (A) Cyclohexyl 3-nitro-4-chlorobenzoate Ten grams (0.05 mole) of 3-nitro-4chlorobenzoic acid, 50 ml. of benzene, 13 g. (0.1 mole) of oxalyl chloride and 3 drops of pyridine were stirred at room temperature for about one hour. The mixture was warmed to 55° C to obtain a homogenous solution. The reaction mixture was evaporated in vacuo to yield an oil. Under vacuum the oil crystallized to yield 12 g. of 3-nitro-4-chlorobenzoyl chloride.

Twelve grams (0.055 mole) fo crude 3-nitro-4-chlorobenzoyl chloride were dissolved in 200 ml. of benzene. 8 milliliters of pyridine were added to the reaction mixture. 6 milliliters of cyclohexanol were dissolved in 50 ml. of benzene and the solution was added dropwise to the acid chloride-pyridine mixture. The reaction mixture was refluxed for 4 hours and filtered. The benzene filtrate was washed successively with dilute acid, dilute base and water. The washed benzene solution was dried and evaporated in vacuo to yield 12.5 g (88 percent) of cyclohexyl 3-nitro-4-chlorobenzoate, mp 57°–58° C.

Analysis $C_{13}H_{24}ClNO_4$ MW 283.5; Calcd: C, 55.04; H, 4.97; N, 4.94; Found: C, 54.90; H, 5.15; N, 5.14.

B. Cyclohexyl 3-nitro-4-dibenzylaminobenzoate

Two and eight-tenths grams (0.01 mole) of cyclohexyl 3-nitro-4-chlorobenzoate, 4.4 ml. (0.022 mole) of dibenzylamine and 20 ml. of dimethylformamide (DMF) were refluxed for six hours. The reaction mixture was evaporated in vacuo and the residue was diluted with 500 ml. of water. The aqueous mixture was extracted with ethyl acetate. The ethyl acetate solution was dried and evaporated in vacuo to give an oil. The oil was taken up in ether and filtered. The solution was evaporated in vacuo to yield 4.2 g. (95 percent) of cyclohexyl 3-nitro-4-dibenzylaminobenzoate as an oil.

C. Cyclohexyl 2-Amino-5(6)-benzimidazolecarboxylate

One hundred grams (0.386 mole) of cyclohexyl 3-nitro-4-dibenzylaminobenzoate were hydrogenated at 60° C for 22 hours with 25 g. of palladium-on-carbon in 875 ml. of 2B ethanol. The catalyst was filtered and the filtrate was evaporated in vacuo to leave an oil. The oil was taken up in ethyl acetate and filtered. Anhydrous HCl gas was passed over the surface of the ethyl acetate solution with stirring. The precipitated o-phenylenediamine hydrochloride salt was collected and washed with anhydrous ether to yield 24.3 g. of product. The salt was dissolved in water and the pH of the aqueous solution was adjusted to 7.00 with 1N sodium hydroxide (130 ml.). Forth milliliters of methanol and 9 g. (0.0845 mole) of cyanogen bromide were added to the aqueous solution. The reaction mixture was stirred overnight. The aqueous mixture was basified with 1N sodium hydroxide and extracted with ethyl acetate. The ethyl acetate extract was decolorized with carbon and filtered. The ethyl acetate solution was evaporated in vacuo to yield 16 g. (73 percent yield based on cyanogen bromide) of cyclohexyl 2-amino-5(6)-benzimidazolecarboxylate as an oil.

EXAMPLE 3 t-Butyl 1-(Dimethylsulfonylamino)-2-Amino-5(6)-Benzimidazolecarboxylate

A. t-Butyl 3,4-Dinitrobenzoate

Fifty-three grams (0.25 mole) of 3,4-dinitrobenzoic acid, 500 ml. of benzene, 65 g. (0.51 mole) of oxalyl chloride and 1 ml. of pyridine were reacted according to Example 2 (A), first paragraph, to provide 3,4-dinitrobenzoyl chloride as a crude oil.

The crude 3,4-dinitrobenzoyl chloride, 500 ml. of benzene, 25 ml. of pyridine and 22 g. (0.3 mole) of t-butyl alcohol were reacted as in Example 2 (A), second paragraph, to provide 33 g. (49 percent yield) of t-butyl 3,4-dinitrobenzoate.

Analysis $C_{11}H_{12}N_2O_6$ MW 268; Calcd: C, 49.26; H, 4.51; N, 10.44; Found: C, 48.95; H, 4.30; N, 10.14.

B. t-Butyl 2-amino-5(6)-benzimidazolecarboxylate

Four and two-tenths grams (0.02 mole) of t-butyl 3,4-dinitrobenzoate were hydrogenated in 95 ml. of ethanol with 1 g. of 5 percent palladium-on-carbon for one hour at room temperature. The exothermic reaction reached a maximum temperature of 45° C with a hydrogen uptake which was 85 percent of theoretical. The catalyst was filtered and the filtrate was evaporated in vacuo to a residual oil. The crude t-butyl 3,4-diaminobenzoate product (0.017 mole) was taken up in a mixture of 20 ml. of methanol and 200 ml. of water. Cyanogen bromide, 1.8 g. (0.017 mole), was reacted with the diamine ester according to the method of Example 2(C) to yield 1.5 g. (38 percent yield) of t-butyl 2-amino-5(6)-benzimidazolecarboxylate.

C. t-Butyl 1-(dimethylaminosulfonyl)-2-amino-5(6)-benzimidazolecarboxylate

Three grams (0.013 mole) of t-butyl 2-amino-5(6)-benzimidazolecarboxylate, 50 ml. of dimethoxyethane, 0.7 g. of 50 percent sodium hydride and 1.9 g. of dimethylsulfamoyl chloride were refluxed for 3 hours. The reaction mixture was filtered and the filtrate was evaporated to dryness in vacuo. The product residue was treated with water and the mixture was extracted with ethyl acetate. The extract was dried ($Na_2SO_4$) and concentrated by boiling on the steam bath until incipient crystallization. The ethyl acetate mixture was cooled in an ice bath and the crystalline product, t-butyl 1-(dimethylaminosulfonyl)-2-amino-5(6)-benzimidazolecarboxylate, was filtered.

EXAMPLE 4

Butyl 2-Amino-5-Benzimidazolecarboxylate

Eleven grams (53 mmoles) of butyl 3,4-diaminobenzoate and 5.7 g. (53 mmoles) of cyanogen bromide were stirred overnight in 300 ml. of water. The reaction mixture was neutralized with dilute base and was diluted with 600 ml. of water. The aqueous phase was extracted with ethyl acetate. The extract was decolarized with carbon and the solvent was evaporated to dryness in vacuo. The residue was triturated with ethyl acetate to yield 11 g. of butyl 2-amino-5-benzimidazolecarboxylate, m.p. about 183°–185° C.

Analysis $C_{12}H_{15}N_3O_2$ MW 233; Calcd: C, 61.79; H, 6.48; Found: C, 61.61; H, 6.63;

EXAMPLE 5

Ethyl 2-Methylamino-5-Benzimidazolecarboxylate

A. Preparation of a mixture of Ethyl 3-amino-4-(3-methyl 2-thioureido)benzoate and Ethyl 4-amino-3-(3-methyl-2-thioureido)benzoate.

Twelve grams (0.1 mole) of ethyl 3,4-diaminobenzoate were dissolved in 300 ml. of acetone with stirring. One tenth mole, 7.3 g., of methylisothiocyanate in acetone was added to the reaction mixture. The mixture was refluxed for 20 hours. After cooling, the mixture was evaporated in dryness in vacuo. The residue was washed with ether and the product was collected to yield 12 g. of the thiourea mixture. The isomeric mixture was characterized by NMR and used in the following step.

B. Preparation of Ethyl 2-methylamino-5-benzimidazolecarboxylate.

About 10 grams of 3A molecular sieve were added to 150 ml. of 2B ethanol and the mixture was stirred for about one-half hour before further additions. Five grams of the thiourea mixture (A) were added followed by the addition of 5 g. of yellow mercuric oxide. The reaction mixtue was refluxed for 16 hours with brisk stirring. After cooling, the mixture was filtered. The filtrate was evaporated to dryness in vacuo. The residue was taken up in ethyl acetate and filtered. The filtrate was concentrated by boiling to one-third the original volume. The product crystallized upon cooling to yield 300 mg. of ethyl 2-methylamino-5-benzimidazolecaboxylate, m.p. about 247°–249° C.

Analysis $C_{11}H_{13}N_3O_2$ MW 219; Calcd: C, 60.45; H, 5.54; Found: C, 59.96; H, 6.14.

EXAMPLE 6

2-(2-Aminobenzimidazole-5-yl)propionic acid

A. 2(3-Nitro-4-acetamidophenyl)propionitrile

One hundred grams of 2-(4-aminophenyl)propionitrile was acetylated with acetic anhydride in pyridine at 100° C. for one hour. After recovery of the product, crystallization from ethanol yielded 113 g. of 2-(4-acetamidophenyl)propionitrile, m.p. about 82°–84° C.

One equivalent, 42 ml., of 70 percent nitric acid was added to 300 ml. of acetic anhydride cooled to 10° C. The acid solution was cooled by means of an ice-salt bath while 125 g. of the acetamido compound was added over a period of about 3–5 minutes with efficient stirring. During the addition the reaction temperature rose to about 25° C. for about 10 minutes. The mixture was stirred at 100° C. for two hours and then allowed to come to room temperature for 3 hours. The mixture was poured onto 500 g. of ice and the ice was allowed to melt. The insoluble product was filtered, dried, and recrystallized from ethanol-carbon tetrachloride to yield 96 g. of 2-(3-nitro-4-acetamidophenyl)-propionitrile, m.p. about 98°–99° C., yellow crystals.

B. 2-(3-Nitro-4-aminophenyl)propionic acid

Forty grams of 2-(3-nitro-4-acetamidophenyl)-propionitrile and 100 ml. of concentrated hydrochloric acid were refluxed under nitrogen for 4 hours. The cooled acid solution was filtered and the filtrate was brought to pH 5 with 50 percent sodium hydroxide. The propionic acid product was filtered, washed with cold water and dried to yield 36 g. of 2-(3-nitro-4-aminophenyl)propionic acid m.p. about 126°–127° C.

C. 2-(3,4-Diaminophenyl)propionic acid

Four grams of the nitro acid obtained above was dissolved in 150 ml. of ethanol and 25 ml. of water. The mixture was hydrogenated at 60 psi at room temperature over 250 mg. of 10 percent palladium-on-carbon. The catalyst was filtered and the filtrate was evaporated to dryness. The residue was crystallized from ethanol after carbon treatment to yield 2-(3,4-diaminophenyl)propionic acid, m.p. 142°–145° C., dec.

D. 2-(2-Aminobenzimidazol-5-yl)propionic acid

The diamino acid obtained above, 7.75 g., was dissolved in 300 ml. of water and the solution was cooled to 15° C. One equivalent of cyanogen bromide, 4.55 g., was added with stirring. Precipitation of solid occurred during the addition, but the solid dissolved completely within about 3 hours. Later, a different solid precipitated. The second solid (I) was filtered, washed with water and was dried. The yield of solid I was 1.6 g. The filtrate was brought to pH 6 with 50 percent sodium hydroxide. A yellow solid (II) precipitated. Solid II was filtered, washed with water, and dried to yield 5.8 g. Solids I and II were identical, yielding 7.4 g. of 2-(2-aminobenzimidazol-5-yl)propionic acid, m.p. about 300° C.

EXAMPLE 7

2-Amino-5-Trifluoromethylbenzimidazole (A) 3,4-Diaminobenzotrifluoride

Eight grams of 5 percent palladium-on-carbon and 275 g. of 3-nitro-4-aminobenzotrifluoride were added to 1.2 l. of 2B ethanol. The nitro compound was reduced under 60 psi of hydrogen with Raney nickel at room temperature for 1 hour. The reduction was exothermic. The catalyst was filtered and the filtrate was evaporated to dryness in vacuo. The product was crystallized from ethanol-water to yield 135 g. of 3,4-diaminobenzotrifluoride, m.p. 51°–53° C.

B. 2-Amino-5-trifluoromethylbenzimidazole

One hundred seventy grams (0.96 m.) of 3,4-diaminobenzotrifluoride obtained above were suspended in 1.3 l. of water. Cyanogen bromide, 101.7 g. (0.96 m.), was added portionwise to the stirred mixture while the reaction temperature was maintained below 45° C. by means of an ice bath. The mixture was stirred overnight at room temperature. The reaction mixture was filtered. Sodium hydroxide, 38.40 (0.96 m.) in 500 ml. of water, was added to the filtrate. The basic filtrate was extracted with ethyl acetate. The extract was washed with water and dried (MgSO$_4$). The ethyl acetate solution was evaporated in vacuo to a small volume and n-hexane was added to induce crystallization of the product. The yield of 2-amino-5-trifluoromethylbenzimidazole was 173.7 g., m.p. 143°–149° C.

EXAMPLE 8

2-Amino-5-Methylsulfonylbenzimidazole

A. 4-Methylsulfonyl-o-phenylenediamine

Eighty grams of (p-chlorophenyl) methyl sulfone was nitrated with 64 g. of nitric acid in 400 ml. of concentrated sulfuric acid. After recovery of the crude product, the nitro sulfone, had m.p. 110°–120° C.

Ninety-five grams of the crude (3-nitro-4-chlorophenyl) methyl sulfone was ammoniated with 200 ml. of liquid ammonia in 200 ml. of 2B ethanol in a sealed autoclave at 150° C. for 6 hours. After cooling and venting the autoclave, the reaction mixture was poured into water. The precipitated product was filtered and recrystallized from ethanol-acetone to yield 53.4 g. of (3-nitro-4-aminophenyl) methyl sulfone, m.p. 197°–199° C.

Forty-nine grams of the (3-nitro-4-aminophenyl) methyl sulfone were dissolved in 1 l. of ethanol and 1.5 g. of 5 percent Ruthenium-on-carbon were added with stirring. Twenty-three grams of hydrazine hydrate are added and the mixture was refluxed for 1 hour. The catalyst was filtered and the filtrate was evaporated to dryness in vacuo. Water was added to the residue, and the product was recovered by filtration to yield 33.6 g. of 4-methylsulfonyl-o-phenylenediamine, m.p. 156°–157° C.

B. 2-Amino-5-methylsulfonylbenzimidazole

One mole, 186.1 g., of 4-methylsulfonyl-o-phenylenediamine was suspended in 1.2 l. of water with stirring. One mole, 106 g., of cyanogenbromide was added portionwise to the reaction mixture. The reaction mixture was stirred for 4 hours and then filtered. Sodium hydroxide, 39 g. (1 m.) in 500 ml. of water, was added to the filtrate. The aqueous mixture was cooled in an ice bath and the product crystallized. The product was collected and dried before crystallization from ethanol-ether; yield 200 g., m.p. 233°–238° C.

EXAMPLE 9

2-Amino-5-Cyanobenzimidazole

A. 4-Acetamidobenzonitrile

One mole (118 g.) of p-aminobenzonitrile was dissolved in 200 ml. of pyridine. One mole (103 g.) of acetic anhydride was added to the pyridine solution and the reaction mixture was warmed on the steam bath (80° C.) for about 90 minutes. The mixture solidified completely. Cold water was added to the solid and the product was broken up and poured into 2 l. of water. The product was filtered and the filter cake was broken up and washed with 1N hydrochloric acid to extract starting material. The acid washed product was collected and washed again with cold water until the washings tested neutral. The neutral product was collected and dried to yield 149 g. of 4-acetamidobenzonitrile, m.p. 205°–207° C.

B. 3-Nitro-4-acetamidobenzonitrile

Sixty-seven grams of potassium nitrate were gradually stirred into 300 ml. of concentrated sulfuric acid at 9° C. to form a paste. Fifty grams of 4-acetamidobenzonitrile were added portionwise to the cold acid mixture. The reaction mixture was maintained at −5° C. for about 1 hour. The thick mixture was poured onto cracked ice. The product was collected and washed with cold water. The wet solid was added portionwise to about 400 ml. of warm acetic anhydride very carefully. Water was added to destroy the excess anhydride. The nitro product was collected and recrystallized from ethanol to yield 25.5 g. of 3-nitro-4-acetamidobenzonitrile m.p. 127°–129° C. A second crop, 23 g., was obtained.

C. 3-Nitro-4-aminobenzonitrile

One-tenth mole (20.5 g.) of 3-nitro-4-acetamidobenzonitrile was dissolved in 0.5 l. of methylene chloride and 10 g. of dry pyridine. Phosphorus pentachloride (22.5 g.) was added and the reaction mixture was stirred at room temperature for 3 hours. The mixture was cooled to 0° C. and 51 ml. of isobutanol were added dropwise to the cold mixture. The mixture was allowed to come to room temperature and the solvents were evaporated to dryness in vacuo. The residue was crystallized from water to yield 12.5 g. of 3-nitro-4-aminobenzonitrile, m.p. 154.5°–156° C.

D. 2-Amino-5-cyanobenzimidazole

3-Nitro-4-aminobenzonitrile (12.5 g.) was hydrogenated at 60 psi with Raney nickel in ethyl acetate at room temperature. The catalyst was filtered and the filtrate was evaporated to dryness in vacuo to provide the crude diamine.

The crude 3,4-diaminobenzonitrile (13.3 g.) was stirred in 450 ml. of water. Cyanogen bromide (10.6 g.) was added and the mixture was stirred at room temperature for 3 hours. The reaction mixture rose to 27° C. After reaction, the mixture was filtered to remove some tarry material. The filtrate was basified with sodium carbonate. The basic solution was filtered to remove any dark material, and the filtrate was extracted with ethyl acetate. The ethyl acetate extract was evaporated in vacuo. The residue was crystallized from ethyl acetate-n-hexane to yield 6.4 g. of 2-amino-5-cyanobenzimidazole, m.p. 223°–226° C.

Analysis $C_8H_6N_4$ MW 158; Calcd: C, 60.75; H, 3.82; Found: C, 60.26; H, 4.04.

EXAMPLE 10

Ethyl 1-Dimethylaminosulfonyl-2-Amino-6-benzimidazolecarboxylate.

Fifty grams (0.24 mole) of ethyl 2-amino-5(6)-benzimidazolecarboxylate, 200 ml. of acetone and 50 ml. of triethylamine were stired together. Dimethylsulfamoyl chloride, 35.8 g. (0.25 mole), was added dropwise to the reaction mixture. The reaction mixture was refluxed for 100 hours. The precipitated product was filtered, washed with water, and recrystallized from methanol to give 15 g. (20 percent yield of ethyl 1-dimethylaminosulfonyl-2-amino-6-benzimidazolecarboxylate.

Analysis $C_{12}H_{15}N_4SO_4$ MW 312; Calcd: C, 46.29; H, 4.86; N, 18.00; Found: C, 46.06; H, 5.10; N, 17.78;

EXAMPLE 11

Ethyl 1-Dimethylaminosulfonyl-2-Acetamido-6-benzimidazolecarboxylate.

Three grams (9.6 mmole) of ethyl 1-dimethylaminosulfonyl-2-amino-6-benzimidazolecarboxylate were stirred overnight with 30 ml. of acetic anhydride. The thick product slurry was poured into water. The product was filtered, washed with water and dried to yield 3 g. (88 percent) of ethyl 1-dimethylaminosulfonyl-2-acetamido-6-benzimidazolecarboxylate, m.p. 155°–157° C.

Analysis $C_{14}H_{18}N_4O_5S$ MW 354; Calcd: C, 47.45; H, 5.12; N, 15.81; Found: C, 47.48; H, 5.16; N, 15.60.

EXAMPLE 12

Ethyl 1-Isopropylsulfonyl-2-Amino-5(6)-Benzimidazolecarboxylate.

Five grams (25.0 mmole) of ethyl 2-amino-5-benzimidazolecarboxylate and 3 ml. of triethylamine were stirred with 150 ml. of acetone. Isopropylsulfonyl chloride, 3.6 g. (25.0 mmole) dissolved in 10 ml. of acetone, was added dropwise to the stirred reaction mixture. The mixture was refluxed for 20 hours. After cooling, the mixture was filtered and the filtrate was evaporated to dryness in vacuo. The residue was taken up in a minimum amount of methanol and allowed to stand overnight at room temperature. The crystalline product was filtered and the material was washed with a small amount of cold methanol and ether. A second crop was obtained from the combined washings to yield 280 mg. of ethyl 1-(isopropylsulfonyl)-2-amino-6-benzimidazolecarboxylate, m.p. about 165°–167° C., colorless crystals. The material was established as the 6-isomer by nuclear magnetic resonance (NMR) in dimethylsulfoxide.

The 5-isomer was recovered from the original methanol filtrate to yield 365 mg. of ethyl 1-isopropylsulfonyl-2-amino-5-benzimidazolecarboxylate, m.p. about 166°–168° C., orange crystals. The structure was confirmed by NMR in dimethylsulfoxide.

Analysis $C_{13}N_{17}N_3O_4S$ MW 311; Calcd: C, 50.15; H, 5.50; N, 13.50; Found: 5-isomer: C, 49.86; H, 5.48; N, 13.24; 6-isomer: C, 49.92; H, 5.26; N, 13.44.

EXAMPLE 13

Ethyl 1-(N-Methyl-N-Ethylaminosulfonyl)-2-Amino-5(6)-Benzimidazolecarboxylate Ten grams (50.0 mmoles) of ethyl 2-amino-5-benzimidazolecarboxylate and 10 ml. of triethylamine were stirred in 40 ml. of dry acetone. Eight grams (50.0 mmoles) of N-methyl-N-ethylsulfamoyl chloride were added and the mixture was refluxed for 48 hours. The reaction mixture was filtered after cooling and the filtrate was concentrated to one-half the original volume in vacuo. The mixture of isomers crystallized from solution upon standing overnight. The product mixture was collected and washed with a small amount of cold methanol.

Analysis $C_{12}H_{28}N_4O_4S$ MW 326; Calcd: C, 47.84; H, 5.56; N, 17.17; Found: C, 48.09; H, 5.49; N, 16.97.

EXAMPLE 14.

Separation of Ethyl 1-(N-Methyl-N-Ethylaminosulfonyl)-2-Amino-6-Benzimidazolecarboxylate by basic hydrolysis.

Four and six-tenths grams (14 mmoles) of an isomeric mixture of ethyl 1-(N-methyl-N-ethylaminosulfonyl-2-amino-5(6)-benzimidazolecarboxylate, 1.7 g. (30 mmoles) of potassium hydroxide and 50 ml. of water and were refluxed for 45 minutes with stirring. After cooling, the insoluble 6-isomer ethyl ester was collected by filtration. The yield was 450 mg. of ethyl 1-(N-methyl-N-ethylaminosulfonyl)-2-amino-6-benzimidazolecarboxylate, m.p. about 170°–171° C.

Analysis $C_{12}N_{18}N_4O_4S$ MW 326; Calcd: C, 47.84; H, 5.56; N, 17.17; Found: C, 47.76; H, 5.66; N, 16.95.

The basic filtrate was neutralized with 1N hydrochloric acid. The solid which precipitated was collected to yield 2 g. of 1-(N-methyl-N-ethylaminosulfonyl)-2-amino-5-benzimidazolecarboxylate as a monohydrate, m.p. about 197°–199° C.

Analysis $C_{11}H_{14}N_4S.H_2O$ MW 316; Calcd: C, 41.77; H, 5.07; N, 17.72; Found: C, 42.62 H, 4.49; N, 17.89.

Further acidification of the neutral filtrate provided a mixture of 5 and 6 carboxylic acids in small amount.

EXAMPLES 15 and 16.

1-Dimethylaminosulfonyl-2-Amino-5(6)-Benzimidazolecarboxamide

A. 1-Dimethylaminosulfonyl-2-amino-5(6)-benzimidazolecarboxylic acid hydrazide.

Three grams of ethyl 1-dimethylaminosulfonyl-2-amino-5(6)-benzimidazolecarboxylate (Ex. 10), 50 ml. of methanol and 6 ml. of hydrazine hydrate were refluxed for about 100 hours. The hydrazide product crystallized out of solution during the reaction. The hot reaction mixture was filtered to yield 200 mg. of 1-dimethylaminosulfonyl-2-amino-5-benzimidazolecarboxylic acid hydrazide, m.p. about 229°–230° C. dec, confirmed by nuclear magnetic resonance spectrum.

Analysis $C_{10}H_{14}N_6O_3S$ MW 298; Calcd: C, 40.30; H, 4.70; N, 28.20; Found: C, 40.21; H, 4.54; N, 28.33.

Upon cooling, the filtrate yielded a solid which was collected. The solid was a mixture of isomeric acid hydrazides. The subsequent filtrates yielded two crops of crystals upon concentrating the cooling to give a combined yield of 350 mg. of 1-dimethylaminosulfonyl-2-amino-6-benzimidazole carboxylic acid hydrazide hydrate, m.p. about 205°–206° C., confirmed by NMR.

Analysis $C_{10}H_{14}N_6O_3S.H_2O$ MW 316; Calcd: C, 37.97; H, 5.06; N, 26.58; Found: C, 38.40; H, 4.41; N, 26.15.

B. 1-Dimethylaminosulfonyl-2-amino-5-benzimidazolecarboxamide hydrate

Two grams of 1-dimethylaminosulfonyl-2-amino-5-benzimidazolecarboxylic acid hydrazide, 8 g. of Raney nickel and 100 ml. of 2B ethanol were refluxed for 4 hours. The cooled mixture was filtered and the catalyst was washed with ethanol. The ethanol washings were combined with the filtrate. The ethanol solution was evaporated to dryness in vacuo. The residue was dissolved in methanol and the solution was filtered through a fritted glass funnel having 4 mm. layer of alumina. The methanol filtrate was concentrated in vacuo to provide 1-dimethylaminosulfonyl-2-amino-5-benzimidazolecarboxamide hydrate, m.p. about 208°–209° C.

Analysis $C_{10}H_{13}N_5O_3S.H_2O$ MW 301; Calcd: C, 39.87; H, 4.98; N, 23.25; Found: C, 40.05; H, 4,78; N, 22.81.

C. 1-Dimethylaminosulfonyl-2-amino-6-benzimidazolecarboxamide.

The procedure of method B above was repeated with 2.5 g. of 1-dimethylaminosulfamoyl-2-amino-6-benzimidazolecarboxylic acid hydrazide and 10 g. of Raney nickel to yield 1-dimethylaminosulfonyl-2-amino-6-benzimidazolecarboxamide, m.p. about 206°–208° C. A second crop was obtained from the mother liquors.

Analysis: $C_{10}H_{13}N_5O_3S$ MW 283; Calcd: C, 42.40; H, 4.63; N, 24.72; Found: Cr- 43.56; H, 4.53; N, 24.60.

EXAMPLE 17

Isobutyl 1-Dimethylaminosulfonyl-2-Acetamido-5(6)-Benzimidazolecarboxylate

A. Six grams (0.018 mole) of 1-dimethylaminosulfonyl-2-acetamido-5(6)-benzimidazolecarboxylic acid obtained from the basic hydrolysis (Ex. 14) of the ethyl ester (Ex. 11), was dissolved in 15 ml. of dimethylformamide (DMF). 1,1'-Carbonyldiimidazole, 3.6 g., was added to the mixture with stirring. Forty fiver milliliters of isobutanol that had been treated with about 200 mg. of sodium hydride was added to the reaction mixture. The reaction was continued at room temperature for about 12 hours. The mixture was poured into 1.2 l. of water. After an initial extraction with n-hexane, the aqueous phase was extracted with ethyl acetate. The ethyl acetate extract was washed with water and dried over molecular sieve. The ethyl acetate solution was evaporated in vacuo to give an isobutanol residue. Ester product crystallized from the isobutanol residue upon standing. The product was crystallized from isobutanol to give 27 g. of the 6-isomer, isobutyl 1-dimethylaminosulfonyl-2-acetamido-6-benzimidazolecarboxylate, m.p. 151°–152° C., confirmed by NMR.

Analysis $C_{16}H_{22}N_4O_5S$ MW 382; Calcd: C, 50.25; H, 5.80; N, 14.43; Found: C,50.46; H, 5.68; N, 14.43.

B. The isobutanol filtrates and mother liquors from the crystallization of the 6-isomer were concentrated to about one-half the original volume in vacuo to yield about 2 g. of the 5-isomer, isobutyl 1-dimethylaminosulfonyl-2-acetamido-5-benzimidazolecarboxylate, m.p. 105°–108° C., confirmed by NMR.

Analysis $C_{16}H_{22}N_4O_5S$ MW 382; Calcd: C, 50.25; H, 5.80; N, 14.43; Found: C, 50.24; H, 5.69; N, 14.89.

EXAMPLE 18

Isobutyl 1-Dimethylaminosulfonyl-2-Amino-6-Benzimidazolecarboxylate

One gram (2.6 mmole) of isobutyl 1-dimethylaminosulfonyl-2-acetamido-6-benzimidazolecarboxylate (Ex. 17) was suspended in 30 ml. of water with 2 pellets (200 mg.) of potassium hydroxide. The mixture was reluxed for 2.5 hours with stirring. The hydrolyzed product was collected to yield 100 mg. of isobutyl 1-dimethylaminosulfonyl-2-amino-6-benzimidazolecarboxylate, m.p. 197°–198° C.

Analysis $C_{14}H_{20}N_4O_4S$ MW 340; Calcd: C, 49.40; H, 5.92; N, 16.46; Found: C, 49.47; H, 5.97; N, 16.56.

EXAMPLE 19

Cyclohexylmethyl 1-Dimethylaminosulfonyl-2-Acetamido-5(6)-Benzimidazolecarboxylate Six grams (0.018 mole) of 1-dimethylaminosulfonyl-2-acetamido-5(6)-benzimidazolecarboxylic acid obtained from the basic hydrolysis of the ethyl ester (Ex. 11). 10 g. of cyclohexylmethanol treated with 200 mg. of 50 percent sodium hydride, and 1,1'-carbonyldiimidazole were reacted in DMF by the method of Example 17 to yield 1 g. of cyclohexylmethyl 1-dimethylaminosulfonyl-2-acetamido-5(6)-benzimidazolecarboxylate as an isomeric mixture.

Analysis $C_{19}H_{26}N_4O_5S$ MW 422; Calcd: C, 54.01; H, 6.20; N, 13.26; Found: C, 53.94; H, 6.01; N, 13.16.

EXAMPLE 20

Benzyl 1-Dimethylaminosulfonyl-2-Amino-5(6)-benzimidazolecarboxylate

One gram (3.1 mmole) of potassium 1-dimethylaminosulfonyl-2-amino-5(6)-benzimidazolecarboxylate was suspended in 10 ml. of dimethylformamide (DMF). Four tenths of a milliliter (3.1 mmole) of benzylchloride in 5 ml. of DMF were added dropwise with stirring. The reaction was stirred at room temperature for about 12 hours. The reaction mixture was decanted from a heavy precipitate and poured into water. Product precipitated from the aqueous solution. An NMR spectrum indicated that both the original precipitate and the aqueous precipitate were the expected benzyl ester. The yield was about 600 mg. (50 percent) of benzyl 1-dimethylaminosulfonyl-2-amino-5(6)-benzimidazolecarboxylate.

Analysis: (1/3 DMF adduct) MW 398; calcd: C, 54.27; H, 5.02; N, 15.33; Found: C, 54.64; H, 4.95; N, 15.95.

EXAMPLES 21–33

The following esters were prepared by the methods of Examples 17–20.

TABLE IV

Esters of 1-Dimethylaminosulfonyl-2-amino-5(6)-benzimidazolecarboxylic acid

| | | MP | Analysis (Percent) | | | | | |
| | | | Theory | | | Found | | |
| No. | Ester* | °C | C | H | N | C | H | N |
| --- | --- | --- | --- | --- | --- | --- | --- | --- |
| 21 | (6)-methyl | 211–213 | 44.29 | 4.73 | 18.78 | 45.28 | 4.72 | 18.21 |
| 22 | propyl | | 47.84 | 5.57 | 17.17 | 47.62 | 5.31 | 16.92 |
| 23 | (6)-isopropyl | 173–175 | 47.84 | 5.56 | 17.17 | 48.08 | 5.42 | 16.96 |
| 24 | (6)-butyl | 150–153 | 49.40 | 5.92 | 16.40 | 49.64 | 5.98 | 16.20 |
| 25 | (6)-isobutyl | 197–198 | 49.40 | 5.92 | 16.46 | 49.67 | 5.97 | 16.56 |
| 26 | (5)-neopentyl | 157–160 | 50.83 | 6.26 | 15.81 | 51.06 | 6.03 | 15.75 |
| 27 | (6)-neopentyl | 196–198 | 50.83 | 6.26 | 15.81 | 50.99 | 6.05 | 15.99 |
| 28 | (6)-cyclohexyl | 180–184 | 52.44 | 6.05 | 15.29 | 52.67 | 6.29 | 15.48 |
| 29 | octyl | | 54.53 | 7.12 | 14.13 | 54.26 | 6.87 | 13.85 |
| 30 | cyclohexylmethyl | | 53.68 | 6.32 | 14.74 | 53.85 | 6.38 | 13.71 |
| 31 | α-methylbenzyl | | 55.66 | 5.19 | 14.42 | 56.83 | 5.41 | 13.87 |
| 32 | allyl | | 48.29 | 4.68 | 17.33 | 48.50 | 4.47 | 17.30 |
| 33 | propargyl | | 48.59 | 4.08 | 17.44 | 48.32 | 4.06 | 17.31 |

*Number indicates ester isomer otherwise the ester is an isomer mixture.

EXAMPLES 34–49

The following esters were prepared by the methods of Examples 17–20.

TABLE V

Esters of 1-Dimethylaminosulfonyl-2-acetamido-5(6)-benzimidazolecarboxylic acid

| No. | | Ester* | MP °C | Theory C | Theory H | Theory N | Found C | Found H | Found N |
|---|---|---|---|---|---|---|---|---|---|
| 34 | (5)- | ethyl | 167–168 | 47.45 | 5.12 | 15.81 | 47.60 | 5.19 | 16.03 |
| 35 | (6)- | ethyl | 201–202 | 47.45 | 5.12 | 15.81 | 47.28 | 5.16 | 15.60 |
| 36 | | isopropyl | | 48.90 | 5.47 | 15.21 | 48.92 | 5.76 | 15.46 |
| 37 | (5)- | isobutyl | 105–108 | 50.25 | 5.80 | 14.65 | 50.24 | 5.69 | 14.89 |
| 38 | (6)- | isobutyl | 151–152 | 50.25 | 5.80 | 14.65 | 50.46 | 5.68 | 14.43 |
| 39 | | sec-butyl | | 50.26 | 5.76 | 14.66 | 49.94 | 5.60 | 14.35 |
| 40 | | cyclobutyl | | 50.52 | 5.30 | 14.73 | 50.39 | 5.08 | 14.56 |
| 41 | | neopentyl | | 51.52 | 6.06 | 14.14 | 51.73 | 5.98 | 14.29 |
| 42 | | cyclohexyl | | 52.93 | 5.92 | 13.72 | 53.04 | 5.68 | 13.90 |
| 43 | (5)- | cyclopropylmethyl | 109–112 | 50.79 | 4.79 | 14.81 | 50.58 | 5.00 | 14.73 |
| 44 | (6)- | cyclopropylmethyl | 146–149 | 50.79 | 4.79 | 14.81 | 50.55 | 5.02 | 14.97 |
| 45 | | 1-cyclopropylethyl | | 51.76 | 5.62 | 14.20 | 51.47 | 5.40 | 14.29 |
| 46 | | cyclohexylmethyl | | 54.01 | 6.20 | 13.26 | 53.94 | 6.01 | 13.16 |
| 47 | | (3-methylcyclohexyl)methyl | | 53.03 | 6.47 | 12.83 | 54.87 | 6.66 | 12.68 |
| 48 | (5)- | phenyl | 167–170 | 53.59 | 4.75 | 13.89 | 53.88 | 4.59 | 13.61 |
| 49 | (6)- | phenyl | 215–220 | 53.59 | 4.75 | 13.89 | 53.73 | 5.03 | 13.79 |

*Number indicates ester isomer otherwise the ester is an isomer mixture.

EXAMPLE 50

1-Dimethylaminosulfonyl-2-Amino-5(6)-N-Ethylbenzimidazolecarboxamide

A. Six grams of 1-dimethylaminosulfonyl-2-acetamido-5(6)-benzimidazolecarboxylic acid were dissolved in 15 ml. of DMG. Three and six-tenths grams of 1,1′-carbonyldiimidazole were added to the stirred mixture. Ethylamine, 20 ml. (excess), was added and the reaction was stirred for about 12 hours. The mixture was poured into a liter of water. The aqueous solution was extracted with ethyl acetate. The ethyl acetate extract was dried over molecular sieve. The ethyl acetate solution was concentrated to a small volume in vacuo. The 6-isomer crystallized to yield 2.5 g. of 1-dimethylaminosulfonyl-2-amino-6-N-ethylbenzimidazolecarboxamide, m.p. 215°–216° C., the 2-acetyl group being lost by aminolysis.

Analysis $C_{14}H_{18}N_5O_4S$ MW 356; Calcd: C, 46.29; H, 5.50; N, 22.49; Found: C, 46.11; H, 5.35; N, 22.25.

B. The 5-isomer was recovered from the ethyl acetate filtrates to yield 2.1 g. of 1-dimethylaminosulfonyl-2-amino-5N-ethylbenzimidazolecarboxamide, m.p. 155°–160° C.

Analysis $C_{14}H_{18}N_5O_4S$ MW 352; Calcd: C, 46.29; H, 5.50; N, 22.49; Found: C, 46.54; H, 5.24; N, 21.93.

EXAMPLE 51

Ethyl 1-(2-Thiophene)sulfonyl-2-Amino-5(6)-benzimidazolecarboxylate

Five and five-tenths grams (0.027m) of ethyl 2-amino-5(6)-benzimidazolecarboxylate were dissolved in 100 ml. of acetone and 3 ml. of triethylamine. Five grams of 2-thiophenesulfonyl chloride dissolved in 10 ml. of acetone were added dropwise to the reaction mixture with stirring. The mixture was reluxed for 24 hours. The amine salt was filtered and the filtrate was evaporated to dryness in vacuo. The residue was recrystallized from methanol to yield 3.6 g. (38 percent) of ethyl 1-(2-thiophene)sulfonyl-2-amino-5(6)-benzimidazolecarboxylate as an isomeric mixture via NMR.

Analysis MW 351; Calcd: C, 47.85; H, 3.73; N, 11.96; Found: C, 47.67; H, 3.84; N, 11.76.

EXAMPLE 52

Ethyl 1-(2-Acetamido-4-methylthiadiazol-5-yl)-sulfonyl-2-Amino-5(6)-benzimidazolecarboxylate Eight and one-tenth grams (0.04m.) of ethyl 2-amino-5(6)-benzimidazolecarboxylate were dissolved in 200 ml. of acetone and 8 ml. of triethylamine. Ten grams (0.04 m.) of 2-acetamido-4-methyl-5-thiadiazolesulfonyl chloride were added dropwise to the reaction mixture with stirring. The mixture was refluxed for 24 (A) was collected by filtration. The precipitate (A) was a (A) was washed with water and dried to yield 2 g. of the 5-isomer of the product, m.p. 209°–210° C. dec. The filtrate was evaporated to dryness in vacuo. The residue was taken up in a small volume of methanol from which 8.5 g. (50 percent yield) of ethyl (1-(2-acetamido-3-methylthiadiazol-5-yl)sulfonyl-2-amino-5(6)-benzimidazolecarboxylate was obtained as an isomeric mixture, m.p. 190°–202° C. dec.

Analysis $C_{15}H_{16}N_6O_5S_2$ MW 423; Calcd: C, 45.39; H, 4.02; N, 16.54; Found: C, 45.52; H, 4.43; N, 15.94.

EXAMPLE 53

Ethyl 1-(2-Methylamino-1,3,4-thiadiazol-5-yl)-sulfonyl-2-amino-5(6)-benzimidazolecarboxylate One and nin-tenths grams (9.3 mmole) of ethyl 2-amino-5(6)-benzimidazolecarboxylate were dissolved in 20 ml. of acetone and 1 ml. of triethylamine. Two grams of 2-methylamino-5-thiadiazolesulfonyl chloride were added dropwise to the reaction mixture with stirring. T the mixture was refluxed for 16 hours. The mixture was filtered and the filtrate was evaporated to dryness in vacuo. The oily residue was taken up in methanol from which ethyl 1-(2-methylamino-1,3,4-thiadiazol-5-yl)sulfonyl-2-amino-5(6)-benzimidazolecarboxylate crystallized as an isomeric mixture.

Analysis $C_{13}H_{14}N_6O_4S_2$ MW 382; Calcd: C, 40.83; H, 3.69; N, 21.98; Found: C, 40.59; H, 3.94; N, 21.78.

EXAMPLE 54

1-Dimethylaminosulfonyl-2-amino-5(6)-hydroxymethylbenzimidazole

A. 2-Amino-5(6)-hydroxymethylbenzimiazole

Twenty-four and six-tenths grams of ethyl 2-amino-5(6)-benzimidazolecarboxylate was suspended in 600 ml. of tetrahydrofuran (THF) under nitrogen. Ninety-six ml. (0.36 mole) of sodium bis(2-methoxyethoxy)-aluminum hydride (RED-Al) in 400 ml. of THF were added dropwise to the stirred reaction mixture at a rate such that the temperature did not exceed 35° C. The mixture was heated at reflux for about 20 hours. The excess RED-AL was decomposed by the addition of 30 ml. of water. The mixture was filtered and the filtrate was evaporated in dryness in vacuo. The foamy residue was treated with 150 ml. of ethyl acetate and 200 ml. of water. The aqueous emulsified phase was separated. The aqueous phase was filtered to yield a yellow solid. The aqueous filtrate was evaporated in vacuo to yield a second crop. The combined yield was 12.3 g. (65 percent) of crude 2-amino-5(6)-hydroxymethylbenzimidazole. An analytical sample of the isomeric mixture was prepared.

Analysis $C_8H_9H_3O$ MW 163; Calcd: C, 58.88; H, 5.56; N, 25.75; Found: C, 58.65; H, 5.48; N, 25.54.

B. 1-Dimethylaminosulfonyl-2-amino-5(6)-hydroxymethylbenzimidazole

Thirty millimoles, 4.9 g., of 2-amino-5(6)-hydroxymethylbenzimidazole was dissolved in 40 ml. of acetone. Thirty millimoles, 3.03 g., of triethylamine were added to the acetone solution followed by 4.32 g. (30 mmoles) of dimethylsulfamoyl chloride. The mixture was heated at reflux for about 17 hours. The mixture was poured into 25 ml. of water. The aqueous mixture was extracted with chloroform. The chloroform extract was washed successively with water and saturated sodium chloride solution. The chloroform solution was filtered and dried. The chloroform was evaporated to dryness in vacuo, to yield 5.5 g. (66 percent) of crude product as an isomeric mixture.

Seven grams of crude isomeric mixture were chromatographed over Woelm silica gel using ethyl acetate as the eluant. The 6-isomer was collected after 6 l. of eluant had passed over the column. The yield was 1.02 g. of 1-dimethylaminosulfonyl-2-amino-6-hydroxymethylbenzimidazole, m.p. 182°–183° C. (ethylacetate-methanol)

Analysis $C_{10}H_{14}N_4O_3S$ MW 270; Calcd: C, 44.43; H, 5.22; N, 20.73; Found: C, 44.37; H, 5.18; N, 20.44.

We claim:

1. A compound of the formula

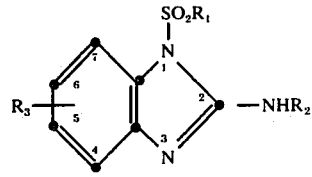

wherein
$R_1$ is $R_4R_5NH$-, wherein $R_4$ and $R_5$ are independently $C_1$-$C_3$ alkyl and when taken together with the nitrogen atom to which they are attached, are pyrrolidino, piperidino or morpholino;
$R_2$ is hydrogen, formyl, acetyl or propionyl;
$R_3$ is $C_1$-$C_8$ alkoxycarbonyl, allyloxycarbonyl, propargyloxycarbonyl, ($C_3$-$C_7$ cycloalkyl)oxycarbonyl, ($C_3$-$C_7$ cycloalkyl)methyloxycarbonyl, 1-($C_3$-$C_7$ cycloalkyl) ethyloxycarbonyl, benzyloxycarbonyl, α-methylbenzyloxycarbonyl, phenoxycarbonyl, hydrazinocarbonyl, carboxy, carboxamido, N-($C_1$-$C_4$ alkyl)carboxamido, N-($C_1$-$C_4$ alkoxy)carboxamido or cyano; and $R_3$ is at the 5 or 6 position.

2. A compound of claim 1 wherein $R_1$ is $R_4R_5N$- and $R_4$ and $R_5$ are $C_1$-$C_3$ alkyl, $R_2$ is hydrogen and $R_3$ is an oxycarbonyl group selected from $C_1$-$C_8$ alkoxycarbonyl, allyloxycarbonyl, propargyloxycarbonyl, ($C_3$-$C_7$ cycloalkyl)oxycarbonyl, ($C_3$-$C_7$ cycloalkyl)methyloxycarbonyl, 1-($C_3$-$C_7$ cycloalkyl)ethyloxycarbonyl, benzyloxycarbonyl, α-methylbenzyloxycarbonyl or phenoxycarbonyl.

3. The compound of claim 2 which is ethyl 1-dimethylaminosulfonyl-2-amino-5(6)-benzimidazolecarboxylate, 4. The compound of claim 2 which is isopropyl 1-dimethylaminosulfonyl-2-amino-5(6)-benzimidazolecarboxylate.

5. The compound of claim 2 which is t-butyl 1-dimethylaminosulfonyl-2-amino-5(6)-benzimidazolecarboxylate.

6. The compound of claim 2 which is neopentyl 1-dimethylaminosulfonyl-2-amino-5(6)-benzimidazolecarboxylate.

7. The compound of claim 2 which is cyclobutyl 1-dimethylaminosulfonyl-2-amino-5(6)-benzimidazolecarboxylate.

8. The compound of claim 2 which is cyclohexyl 1-dimethylaminosulfonyl-2-amino-5(6)-benzimidazolecarboxylate.

9. The compound of claim 2 which is 1-dimethylaminosulfonyl-2-amino-5(6)-benzimidazolecarboxylic acid, 1-(cyclopropyl)ethyl ester.

10. The compound of claim 2 which is ethyl 1-(N-methyl-N-ethylaminosulfonyl)-2-amino-5(6)-benzimidazolecarboxylate.

11. The compound of claim 2 which is ethyl 1-(N-methyl-N-propylaminosulfonyl)-2-amino-5(6)-benzimidazolecarboxylate.

12. The compound of claim 2 which is ethyl 1-diethylaminosulfonyl-2-amino-5(6)-benzimidazolecarboxylate.

13. A compound of claim 2 wherein $R_3$ is at the 6 position.

14. The compound of claim 13 which is ethyl 1-dimethylaminosulfonyl-2-amino-6-benzimidazolecarboxylate.

15. The compound of claim 13 which is isopropyl 1-dimethylaminosulfonyl-2-amino-6-benzimidazolecarboxylate.

16. The compound of claim 13 which is t-butyl 1-dimethylaminosulfonyl-2-amino-6-benzimidazolecarboxylate.

17. The compound of claim 13 which is neopentyl 1-dimethylaminosulfonyl-2-amino-6-benzimidazolecarboxylate.

18. The compound of claim 13 which is cyclohexyl 1-dimethylaminosulfonyl-2-amino-6-benzimidazolecarboxylate.

19. The compound of claim 13 which is 1-dimethylaminosulfonyl-2-amino-6-benzimidazolecarboxylic acid, 1-(cyclopropyl)ethyl ester.

20. The compound of claim 13 which is cyclobutyl 1-dimethylaminosulfonyl-2-amino-6-benzimidazolecarboxylate.

21. The compound of claim 13 which is ethyl 1-(N-methyl-N-ethylaminosulfonyl)-2-amino-6-benzimidazolecarboxylate.

22. The compound of claim 13 which is ethyl 1-N-methyl-N-propylaminosulfonyl)-2-amino-6-benzimidazolecarboxylate.

23. The compound of claim 13 which is ethyl 1-diethylaminosulfonyl-2-amino-6-benzimidazolecarboxylate.

* * * * *